(12) United States Patent
Shelton, IV

(10) Patent No.: US 7,857,183 B2
(45) Date of Patent: Dec. 28, 2010

(54) SURGICAL INSTRUMENT INCORPORATING AN ELECTRICALLY ACTUATED ARTICULATION MECHANISM

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1380 days.

(21) Appl. No.: 11/095,428

(22) Filed: Mar. 31, 2005

(65) Prior Publication Data

US 2006/0025811 A1 Feb. 2, 2006

(51) Int. Cl.
*A61B 17/072* (2006.01)
(52) U.S. Cl. .................. 227/175.1; 227/19; 227/176.1
(58) Field of Classification Search ............. 227/175.1, 227/176.1, 178.1, 180.1, 19; 600/121; 606/139, 606/142, 219
See application file for complete search history.

(56) References Cited

U.S. PATENT DOCUMENTS

| | | | |
|---|---|---|---|
| 2,711,461 A * | 6/1955 | Happe ................... 200/522 |
| 4,473,077 A | 9/1984 | Noiles et al. |
| 4,543,090 A | 9/1985 | McCoy |
| 4,554,064 A | 11/1985 | McClintock et al. |
| 4,601,705 A | 7/1986 | McCoy |
| 4,753,223 A | 6/1988 | Bremer |
| 4,892,545 A | 1/1990 | Day et al. |
| 5,031,814 A | 7/1991 | Tompkins et al. |
| 5,071,052 A | 12/1991 | Rodak et al. |
| 5,137,198 A | 8/1992 | Nobis et al. |
| 5,171,249 A | 12/1992 | Stefanchik et al. |
| 5,202,914 A | 4/1993 | Kim et al. |
| 5,263,629 A | 11/1993 | Trumbull et al. |
| 5,290,240 A | 3/1994 | Horres, Jr. |
| 5,312,023 A | 5/1994 | Green et al. |
| 5,372,124 A | 12/1994 | Takayama et al. |
| 5,387,194 A | 2/1995 | Williams et al. |
| 5,389,098 A | 2/1995 | Tsuruta et al. |
| 5,397,046 A | 3/1995 | Savage et al. |
| 5,397,324 A | 3/1995 | Carroll et al. |
| 5,399,256 A | 3/1995 | Bohs et al. |
| 5,403,312 A | 4/1995 | Yates et al. |
| 5,413,267 A | 5/1995 | Solyntjes et al. |
| 5,413,268 A | 5/1995 | Green et al. |
| 5,431,668 A | 7/1995 | Burbank, III et al. |
| 5,441,193 A | 8/1995 | Gravener |

(Continued)

FOREIGN PATENT DOCUMENTS

DE 1993372 9/1968

(Continued)

OTHER PUBLICATIONS

EPO Search Report, Application No. 06255058.7, Jan. 31, 2007, pp. 1-3.

(Continued)

*Primary Examiner*—Rinaldi I Rada
*Assistant Examiner*—Nathaniel Chukwurah

(57) ABSTRACT

A surgical instrument particularly suited to endoscopic use articulates an end effector by including an articulation mechanism in an elongate shaft that incorporates an electrically actuated polymer (EAP) actuator for remotely articulating the end effector. In particular, a flexible neck to a frame of the elongate neck may be laterally urged to the left or right by EAP actuators and advantageously locked into an articulated state.

12 Claims, 22 Drawing Sheets

U.S. PATENT DOCUMENTS

| | | |
|---|---|---|
| 5,445,304 A | 8/1995 | Plyley et al. |
| 5,465,895 A | 11/1995 | Knodel et al. |
| 5,468,250 A | 11/1995 | Paraschac et al. |
| 5,484,095 A | 1/1996 | Green et al. |
| 5,503,638 A | 4/1996 | Cooper et al. |
| 5,520,787 A | 5/1996 | Hanagan et al. |
| 5,535,937 A | 7/1996 | Boiarske et al. |
| 5,542,594 A | 8/1996 | McKean et al. |
| 5,549,628 A | 8/1996 | Cooper et al. |
| 5,555,555 A | 9/1996 | Sato et al. |
| 5,562,239 A | 10/1996 | Boiarski et al. |
| 5,584,425 A | 12/1996 | Savage et al. |
| 5,592,668 A | 1/1997 | Harding et al. |
| 5,599,329 A | 2/1997 | Gabbay |
| 5,601,582 A | 2/1997 | Shelton et al. |
| 5,609,285 A | 3/1997 | Grant |
| 5,624,452 A | 4/1997 | Yates |
| 5,634,584 A | 6/1997 | Okorocha et al. |
| 5,635,721 A | 6/1997 | Bardi et al. |
| 5,661,887 A | 9/1997 | Byrne et al. |
| 5,665,285 A | 9/1997 | Hattori et al. |
| 5,667,517 A | 9/1997 | Hooven |
| 5,669,918 A | 9/1997 | Balazs |
| 5,673,840 A | 10/1997 | Schulze et al. |
| 5,673,841 A | 10/1997 | Schulze et al. |
| 5,680,983 A | 10/1997 | Plyley et al. |
| 5,688,270 A | 11/1997 | Yates et al. |
| 5,692,668 A | 12/1997 | Schulze et al. |
| 5,693,042 A | 12/1997 | Boiarski et al. |
| 5,702,409 A | 12/1997 | Rayburn et al. |
| 5,704,534 A * | 1/1998 | Huitema et al. .......... 227/175.1 |
| 5,709,334 A | 1/1998 | Sorrentino et al. |
| 5,735,445 A | 4/1998 | Vidal et al. |
| 5,769,892 A | 6/1998 | Kingwell |
| 5,779,130 A | 7/1998 | Alesi et al. |
| 5,792,165 A | 8/1998 | Klieman et al. |
| 5,797,537 A | 8/1998 | Oberlin et al. |
| 5,810,855 A | 9/1998 | Rayburn et al. |
| 5,826,776 A | 10/1998 | Schulze et al. |
| 5,829,662 A | 11/1998 | Allen et al. |
| 5,855,565 A | 1/1999 | Bar-Cohen et al. |
| 5,865,361 A | 2/1999 | Milliman et al. |
| 5,876,401 A | 3/1999 | Schulze et al. |
| 5,901,895 A | 5/1999 | Heaton et al. |
| 5,902,312 A | 5/1999 | Frater et al. |
| 5,908,427 A | 6/1999 | McKean et al. |
| 5,918,791 A | 7/1999 | Sorrentino et al. |
| 5,959,852 A | 9/1999 | Deloy et al. |
| 5,964,774 A | 10/1999 | McKean et al. |
| 5,972,165 A | 10/1999 | Sethna et al. |
| 6,010,054 A | 1/2000 | Johnson et al. |
| 6,032,849 A | 3/2000 | Mastri et al. |
| 6,033,427 A | 3/2000 | Lee |
| 6,063,097 A | 5/2000 | Oi et al. |
| 6,079,606 A | 6/2000 | Milliman et al. |
| 6,109,500 A | 8/2000 | Alli et al. |
| 6,202,914 B1 | 3/2001 | Geiste et al. |
| 6,241,139 B1 | 6/2001 | Milliman et al. |
| 6,302,311 B1 | 10/2001 | Adams et al. |
| 6,330,965 B1 * | 12/2001 | Milliman et al. .......... 227/176.1 |
| 6,488,197 B1 | 12/2002 | Whitman |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,514,237 B1 | 2/2003 | Maseda |
| 6,545,384 B1 | 4/2003 | Pelrine et al. |
| 6,577,899 B2 | 6/2003 | Lebel et al. |
| 6,583,533 B2 | 6/2003 | Pelrine et al. |
| 6,586,859 B2 | 7/2003 | Kornbluh et al. |
| 6,595,852 B2 | 7/2003 | Wang |
| 6,652,521 B2 | 11/2003 | Schulze |
| 6,656,193 B2 | 12/2003 | Grant et al. |
| 6,667,825 B2 | 12/2003 | Lu et al. |
| 6,669,073 B2 | 12/2003 | Milliman et al. |
| 6,699,245 B2 * | 3/2004 | Dinger et al. ................. 606/49 |
| 6,716,233 B1 | 4/2004 | Whitman |
| 6,740,079 B1 | 5/2004 | Eggers et al. |
| 6,770,027 B2 | 8/2004 | Banik et al. |
| 6,786,382 B1 | 9/2004 | Hoffman |
| 6,830,174 B2 | 12/2004 | Hillstead et al. |
| 6,835,173 B2 | 12/2004 | Couvillon, Jr. |
| 6,840,246 B2 | 1/2005 | Downing |
| 6,905,057 B2 | 6/2005 | Swayze et al. |
| 6,913,579 B2 * | 7/2005 | Truckai et al. .............. 600/564 |
| 6,923,804 B2 | 8/2005 | Eggers et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,988,649 B2 | 1/2006 | Shelton, IV et al. |
| 7,000,819 B2 | 2/2006 | Swayze et al. |
| 7,044,352 B2 | 5/2006 | Shelton, IV et al. |
| 7,055,731 B2 | 6/2006 | Shelton, IV et al. |
| 7,063,699 B2 | 6/2006 | Hess et al. |
| 7,074,217 B2 | 7/2006 | Strul et al. |
| 7,083,075 B2 | 8/2006 | Swayze et al. |
| 7,111,769 B2 | 9/2006 | Wales et al. |
| 7,140,528 B2 | 11/2006 | Shelton, IV |
| 7,143,925 B2 | 12/2006 | Shelton, IV et al. |
| 7,147,138 B2 | 12/2006 | Shelton, IV |
| 7,208,005 B2 | 4/2007 | Frecker et al. |
| 7,213,736 B2 | 5/2007 | Wales et al. |
| 7,238,195 B2 | 7/2007 | Viola |
| 7,338,509 B2 | 3/2008 | Mattison |
| 7,354,447 B2 | 4/2008 | Shelton et al. |
| 7,364,061 B2 | 4/2008 | Swayze et al. |
| 7,367,485 B2 | 5/2008 | Shelton, IV et al. |
| 7,380,696 B2 | 6/2008 | Shelton, IV et al. |
| 7,404,509 B2 | 7/2008 | Ortiz et al. |
| 7,407,074 B2 | 8/2008 | Ortiz et al. |
| 7,431,730 B2 | 10/2008 | Viola |
| 7,506,790 B2 | 3/2009 | Shelton, IV |
| 7,517,356 B2 | 4/2009 | Heinrich |
| 7,559,452 B2 | 7/2009 | Wales et al. |
| 7,607,557 B2 | 10/2009 | Shelton et al. |
| 2001/0029384 A1 | 10/2001 | Nicholas et al. |
| 2002/0068224 A1 | 6/2002 | Danda et al. |
| 2002/0074005 A1 | 6/2002 | Hobb et al. |
| 2002/0165541 A1 | 11/2002 | Whitman |
| 2003/0065358 A1 | 4/2003 | Frecker |
| 2003/0069474 A1 | 4/2003 | Couvillon et al. |
| 2003/0199870 A1 | 10/2003 | Truckai et al. |
| 2003/0236531 A1 | 12/2003 | Couvillon, Jr. |
| 2004/0002726 A1 | 1/2004 | Nunez et al. |
| 2004/0054322 A1 * | 3/2004 | Vargas ..................... 604/95.04 |
| 2004/0097971 A1 | 5/2004 | Hughett |
| 2004/0050971 A1 | 6/2004 | Liddicoat |
| 2004/0138700 A1 * | 7/2004 | Cooper et al. ............... 606/205 |
| 2004/0149802 A1 | 8/2004 | Whitman |
| 2004/0232195 A1 | 11/2004 | Shelton, IV et al. |
| 2004/0232196 A1 | 11/2004 | Shelton et al. |
| 2004/0232197 A1 | 11/2004 | Shelton et al. |
| 2005/0006429 A1 | 1/2005 | Wales et al. |
| 2005/0006431 A1 | 1/2005 | Shelton, IV et al. |
| 2005/0006434 A1 | 1/2005 | Wales et al. |
| 2005/0067457 A1 | 3/2005 | Shelton et al. |
| 2005/0067458 A1 | 3/2005 | Swayze et al. |
| 2005/0085693 A1 | 4/2005 | Belson et al. |
| 2005/0102017 A1 * | 5/2005 | Mattison .................... 623/1.11 |
| 2005/0165415 A1 | 7/2005 | Wales |
| 2005/0173490 A1 | 8/2005 | Shelton |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |

| | | | |
|---|---|---|---|
| 2006/0025810 | A1 | 2/2006 | Shelton, IV |
| 2006/0025811 | A1 | 2/2006 | Shelton, IV |
| 2006/0025812 | A1 | 2/2006 | Shelton, IV |
| 2006/0025813 | A1 | 2/2006 | Shelton, IV et al. |
| 2006/0025816 | A1 | 2/2006 | Shelton, IV |
| 2006/0060630 | A1 | 3/2006 | Shelton, IV et al. |
| 2006/0190028 | A1 | 8/2006 | Wales et al. |
| 2007/0102453 | A1 | 5/2007 | Morgan et al. |

FOREIGN PATENT DOCUMENTS

| | | |
|---|---|---|
| DE | 4015562 | 11/1991 |
| DE | 4303544 | 9/1993 |
| DE | 19534320 | 2/1997 |
| DE | 19537299 | 4/1997 |
| DE | 19643073 | 4/1997 |
| DE | 19647354 | 5/1998 |
| EP | 0 500 353 | 8/1992 |
| EP | 0 674 876 | 10/1995 |
| EP | 0 741 996 | 11/1996 |
| EP | 0741966 | 11/1996 |
| EP | 0 832 605 | 4/1998 |
| EP | 1323384 | 7/2003 |
| EP | 1 522 264 | 4/2005 |
| EP | 1621137 | 2/2006 |
| EP | 1621141 | 2/2006 |
| EP | 1621143 | 2/2006 |
| EP | 1621151 | 2/2006 |
| EP | 1693008 | 8/2006 |
| WO | WO 99/02090 | 1/1999 |
| WO | WO 00/78222 | 12/2000 |
| WO | WO 01/56455 | 8/2001 |
| WO | WO 01/62158 | 8/2001 |
| WO | WO 01/62163 | 8/2001 |
| WO | WO 02/28268 | 4/2002 |
| WO | WO 03/088845 | 10/2003 |
| WO | WO 03/090630 | 11/2003 |
| WO | WO 03/094743 | 11/2003 |
| WO | WO 2004/014238 | 2/2004 |
| WO | WO 2004/050971 | 6/2004 |
| WO | WO 2004/086987 | 10/2004 |

OTHER PUBLICATIONS

EPO Search Report, Application No. 06255062.9, Nov. 23, 2006, pp. 1-3.
EPO Search Report, Application No. 06255053.8, Jan. 25, 2007, pp. 1-3.
EPO Search Report, Application No. 06255057.9, Jan. 29, 2007, pp. 1-3.
EPO Search Report, Application No. 06255064.5, Feb. 9, 2007, pp. 1-3.
EPO Search Report, Application No. 06255065.2, Feb. 15, 2007, pp. 1-3.
U.S. Appl. No. 10/441,362, filed May 20, 2003, Ho.
U.S. Appl. No. 10/441,424, filed May 20, 2003, Shelton IV et al.
U.S. Appl. No. 10/615,971, filed Jul. 9, 2003, Wales et al.
U.S. Appl. No. 10/615,973, filed Jul. 9, 2003, Wales et al.
U.S. Appl. No. 10/673,929, filed Sep. 29, 2003, Shelton IV et al.
U.S. Appl. No. 11/052,387, filed Feb. 7, 2005, Shelton IV et al.
U.S. Appl. No. 11/052,632, filed Feb. 7, 2005, Rao et al.
U.S. Appl. No. 11/066,371, filed Feb. 25, 2005, Shelton IV.
U.S. Appl. No. 11/082,495, filed Mar. 17, 2005, Shelton, IV.
U.S. Appl. No. 11/083,740, filed Mar. 18, 2005, Wales et al.
U.S. Appl. No. 11/162,984, filed Sep. 3, 2005, Ortiz et al.
U.S. Appl. No. 11/162,985, filed Sep. 30, 2005, Ortiz et al.
U.S. Appl. No. 11/162,986, filed Sep. 30, 2005, Ortiz et al.
U.S. Appl. No. 11/162,988, filed Sep. 30, 2005, Ortiz et al.
U.S. Appl. No. 11/162,989, filed Sep. 30, 2005, Ortiz et al.
U.S. Appl. No. 11/162,990, filed Sep. 30, 2005, Ortiz et al.
U.S. Appl. No. 11/162,991, filed Sep. 30, 2005, Ortiz et al.
U.S. Appl. No. 11/162,992, filed Sep. 30, 2005, Ortiz et al.
U.S. Appl. No. 11/240,836, filed Sep. 30, 2005, Shelton IV et al.
U.S. Appl. No. 60/591,694, filed Jul. 28, 2004, Shelton IV.
Non-Final Rejection dated Nov. 13, 2006 for U.S. Appl. No. 11/181,046.
Non-Final Rejection dated Mar. 22, 2007 for U.S. Appl. No. 11/082,495.
Non-Final Rejection dated Aug. 7, 2007 for U.S. Appl. No. 11/162,990.
Non-Final Rejection dated Aug. 29, 2007 for U.S. Appl. No. 11/181,046.
Non-Final Rejection dated Sep. 21, 2007 for U.S. Appl. No. 11/162,986.
Non-Final Rejection dated Sep. 21, 2007 for U.S. Appl. No. 11/162,988.
Notice of Allowance dated May 23, 2006 for U.S. Appl. No. 11/096,158.
Notice of Allowance dated Jul. 25, 2006 for U.S. Appl. No. 11/066,371.
Notice of Allowance dated Aug. 14, 2006 for U.S. Appl. No. 11/157,767.
Notice of Allowance dated Sep. 25, 2006 for U.S. Appl. No. 11/083,740.
Notice of Allowance dated Dec. 1, 2006 for U.S. Appl. No. 10/955,042.
Notice of Allowance dated Aug. 31, 2007 for U.S. Appl. No. 11/096,096.
Notice of Allowance dated Sep. 19, 2007 for U.S. Appl. No. 11/082,495.
Notice of Allowance dated Oct. 1, 2007 for U.S. Appl. No. 10/955,042.
Examination Report for Application 05254680, Sep. 22, 2006.
Examination Report for Application 05254685, Sep. 22, 2006.
Examination Report for Application 05254694, Sep. 22, 2006.
Examination Report for Application 05254695, Sep. 22, 2006.
EPO Search Report, Application No. 05254680.1, Jan. 12, 2006, pp. 1-5.
EPO Search Report, Application No. 05254694.2, Jan. 12, 2006, pp. 1-5.
EPO Search Report, Application No. 05254685.0, Jan. 12, 2006, pp. 1-5.
EPO Search Report, Application No. 05254695.9, Jan. 12, 2006, pp. 1-5.
Guidelines for Hand and Power Tools, http://www.osha.gov/doc/outreachtraining/htmlfiles/tools.html, OSHA, May 1996, p. 3.
Office Action for U.S. Appl. No. 10/955,042 dated Mar. 15, 2006.
Office Action for U.S. Appl. No. 10/955,042 dated Mar. 29, 2007.
Notice of Allowance for U.S. Appl. No. 11/240,836 dated Mar. 13, 2008.
Final Rejection dated Oct. 18, 2006 for U.S. Appl. No. 11/096,096.
Office Action dated Mar. 22, 2007 for U.S. Appl. No. 11/082,495.
Notice of Allowance dated Aug. 22, 2006 for U.S. Appl. No. 11/181,471.
Notice of Allowance dated Sep. 25, 2006 for U.S. Appl. No. 11/083,470.
Notice of Allowance dated Jan. 5, 2007 for U.S. Appl. No. 11/096,096.
Notice of Allowance dated Sep. 12, 2007 for U.S. Appl. No. 11/240,836.
Notice of Allowance dated Mar. 25, 2008 for U.S. Appl. No. 11/096,096.
Notice of Allowance dated Apr. 10, 2008 for U.S. Appl. No. 11/082,495.
Notice of Allowance dated Apr. 10, 2008 for U.S. Appl. No. 11/162,990.
Notice of Allowance dated Apr. 18, 2008 for U.S. Appl. No. 11/162,985.
Notice of Allowance dated Apr. 18, 2008 for U.S. Appl. No. 11/162,986.
Notice of Allowance dated Apr. 18, 2008 for U.S. Appl. No. 11/162,988.
Non-Final Rejection dated May 5, 2008 for U.S. Appl. No. 11/181,046.
Notice of Allowance dated Jun. 10, 2008 for U.S. Appl. No. 11/082,495.

Notice of Allowance dated Jun. 10, 2008 for U.S. Appl. No. 11/240,836.
Notice of Allowance dated Aug. 11, 2008 for U.S. Appl. No. 11/082,495.
EPO Search Report dated Feb. 29, 2008 for U.S. Appl. No. 05254681.9.
EPO Search Report dated Mar. 3, 2008 for U.S. Appl. No. 05254699.1.
EPO Search Report dated Feb. 26, 2008 for U.S. Appl. No. 05254700.7.
EPO Search Report dated Mar. 25, 2008 for Application No. 05254703.1.
European Search Report dated Mar. 27, 2008 for Application No. 05254684.

* cited by examiner

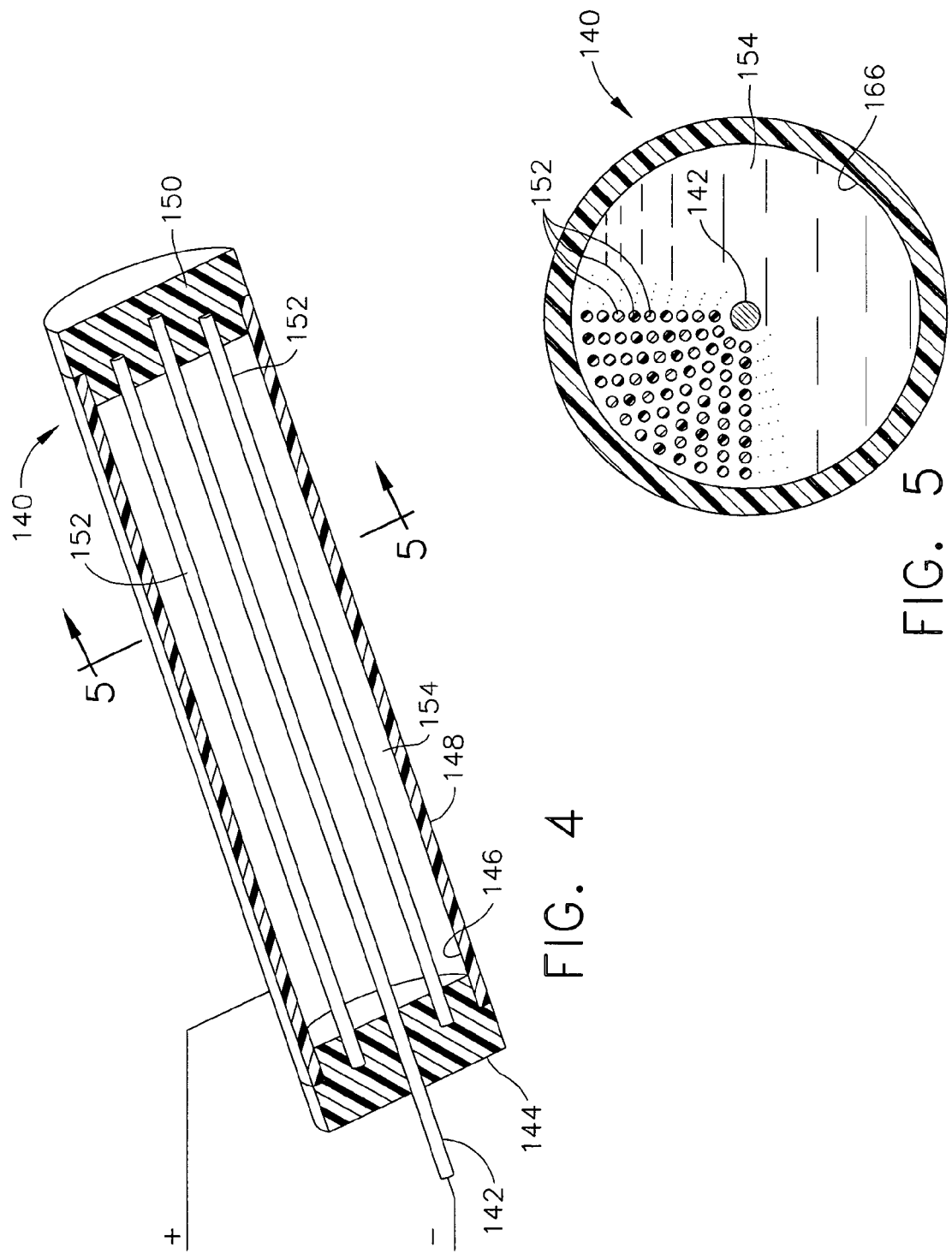

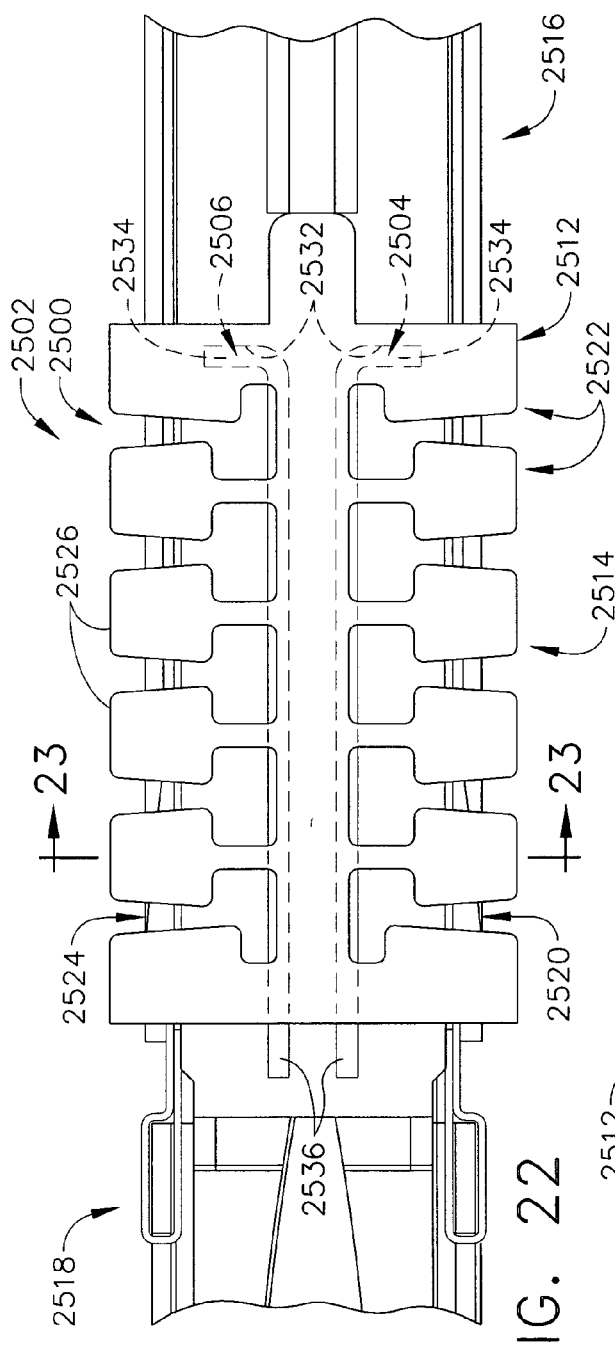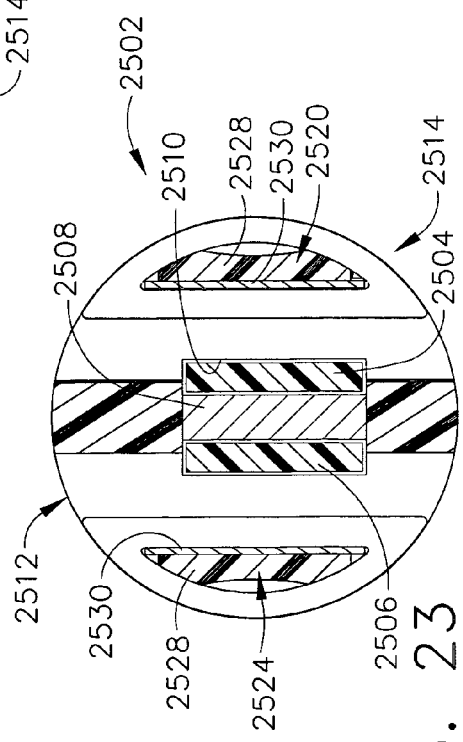
FIG. 22
FIG. 23

SURGICAL INSTRUMENT INCORPORATING AN ELECTRICALLY ACTUATED ARTICULATION MECHANISM

CROSS REFERENCE TO RELATED APPLICATIONS

This application claims the benefit of U.S. provisional application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004.

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and an energy device using ultrasound, RF, laser, etc.) to a surgical site, and more particularly to such surgical instruments with an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally, these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. patent Ser. No. 10/443,617, "SURGICAL STAPLING INSTRUMENT INCORPORATING AN E-BEAM FIRING MECHANISM" to Shelton et al., filed on 20 May 2003, which is hereby incorporated by reference in its entirety, describes an improved "E-beam" firing bar for severing tissue and actuating staples. Some of the additional advantages include affirmatively spacing the jaws of the end effector, or more specifically a staple applying assembly, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

In co-pending and commonly owned U.S. patent application Ser. No. 10/615,973 "SURGICAL INSTRUMENT INCORPORATING AN ARTICULATION MECHANISM HAVING ROTATION ABOUT THE LONGITUDINAL AXIS" to Frederick E. Shelton IV et al, the disclosure of which is hereby incorporated by reference in its entirety, a rotational motion is used to transfer articulation motion as an alternative to a longitudinal motion.

While these mechanically communicated articulation motions have successfully enabled an endoscopic surgical stapling and severing instrument to articulate, development trends pose numerous challenges and barriers to entry into the market. Conflicting design objects include a shaft of as small a diameter as possible to reduce the size of the surgical opening yet sufficient strength to perform the several motions (e.g., closing, firing, articulation, rotation, etc.).

In addition, even though further reduction in cross-sectional size would be desirable, another conflicting desire is to incorporate yet additional functionality at the end effector. For instance, one such additional function is deploying a buttress at the staple site. A buttress is a pair of thin foam or fabric strips that are placed on the anvil and on the cartridge and are stapled into place on either side of the tissue that is transected. It adds structural integrity to the staple line for either extremely thin or thick tissues. Another would be additional enhancements to prevent firing with an improperly closed end effector, empty staple cartridge, missing cartridge, performing a therapeutic or diagnostic treatment by sending energy or fluid to the end effector, etc. Creating sufficient room in the shaft of the instrument to facilitate such additional function creates an incentive to modify how the end effector is articulated.

Consequently, a significant need exists for an articulating surgical instrument that incorporates an articulation mechanism that requires less mechanical mechanisms passing through the shaft of the instrument.

BRIEF SUMMARY OF THE INVENTION

The invention overcomes the above-noted and other deficiencies of the prior art by providing a surgical instrument having an articulating shaft attached between a handle and an end effector. An electroactive polymer (EAP) actuator disposed in an articulation joint of the shaft is responsive to an electrical signal passed through the shaft to effect articulation. Thereby a shaft of advantageously small diameter may be achieved yet with the functionality of remotely controllable actuation.

In one aspect of the invention, a surgical instrument includes an articulating joint attached between an end effector and a distal end of an elongate shaft. An electrical actuator is positioned to actuate the articulation joint in response to an electrical signal remotely produced in a handle proximally attached to the elongate shaft.

In another aspect of the invention, a surgical instrument has an elongate shaft having a frame assembly and an encompassing and a longitudinally, slidingly received closure sleeve assembly. A staple applying assembly includes an elongate channel, a staple cartridge engaged in the elongate channel, and an anvil pivotally attached to the elongate channel presenting a staple forming surface to the staple cartridge. An articulation joint is formed in the frame assembly. In particular, a distal frame portion is attached to the elongate channel and a proximal frame portion is pivotally attached to the distal frame portion. A handle attached to a proximal end of the elongate shaft selectively communicates an electrical signal to the elongate shaft to an electroactive polymer actuator connected to the articulation joint that responds thereto to perform articulation of the staple applying assembly. Thus, a surgical stapling and severing instrument is provided that may approach tissue from a desired angle.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 is a perspective view of a cutaway along a longitudinal axis of a contracting EAP fiber actuator.

FIG. 5 is a front view in elevation taken in cross section along lines 5-5 of the contracting EAP fiber actuator of FIG. 4.

FIG. 22 is a top view of a flexible articulation joint incorporating the EAP support plates of FIGS. 43-46.

FIG. 23 is a front view in elevation of the flexible articulation joint of FIG. 22 taken through lines 23-23.

DETAILED DESCRIPTION OF THE INVENTION

Surgical Instrument With EAP Actuated Flexneck Articulation Joint.

Figure 1:
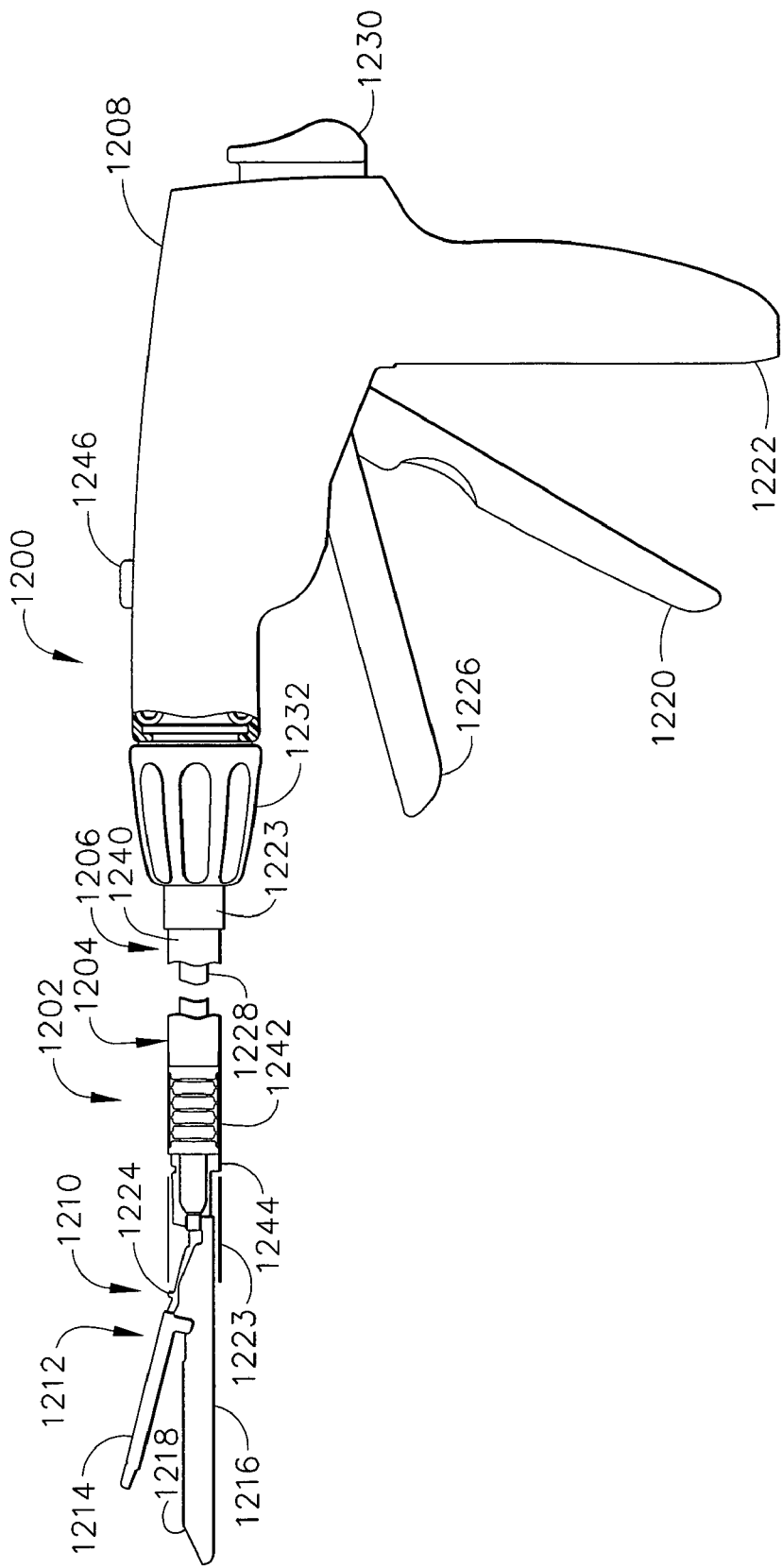
FIG. 1 is a right side view in elevation of a surgical instrument with a closure sleeve assembly cut away to expose an EAP actuated articulation mechanism that articulates a flexible articulating frame ground.

In FIG. 1, a surgical instrument 1200 advantageously incorporates an EAP actuated articulation joint 1202 that is integral to an articulating frame assembly 1204 of an elongate shaft 1206 that transfers separate closure and firing motions from a handle 1208 to an end effector 1210, depicted as a staple applying assembly 1212 having a closeable anvil 1214 that is pivotally attached to an elongate channel 1216 that holds a replaceable staple cartridge 1218. The handle 1208 includes a closure trigger 1220 that is squeezed proximally toward a pistol grip 1222 to effect closure of the anvil 1214. It should be appreciated that a closure sleeve assembly 1223 or other closure means (e.g., EAP actuated anvil, internal longitudinally translating member, etc.) that is not shown acts upon an anvil closure feature 1224 to effect opening and closing of the anvil 1214. Once closed and clamped, a more distal firing trigger 1226 is squeezed toward the pistol grip 1222 to effect firing of a firing member 1228 longitudinally down the elongate shaft 1206 to cause severing of tissue and stapling of the severed ends. Once the firing trigger 1226 is released, a closure release button 1230 is depressed along with a slight depression of the closure trigger 1220 to release clamping components followed by release of the closure trigger 1220 to open the anvil 1214 and allow release of the stapled and severed tissue. A rotation knob 1232 allows selective rotation about a longitudinal axis of the elongate shaft 1206.

Figure 1A:
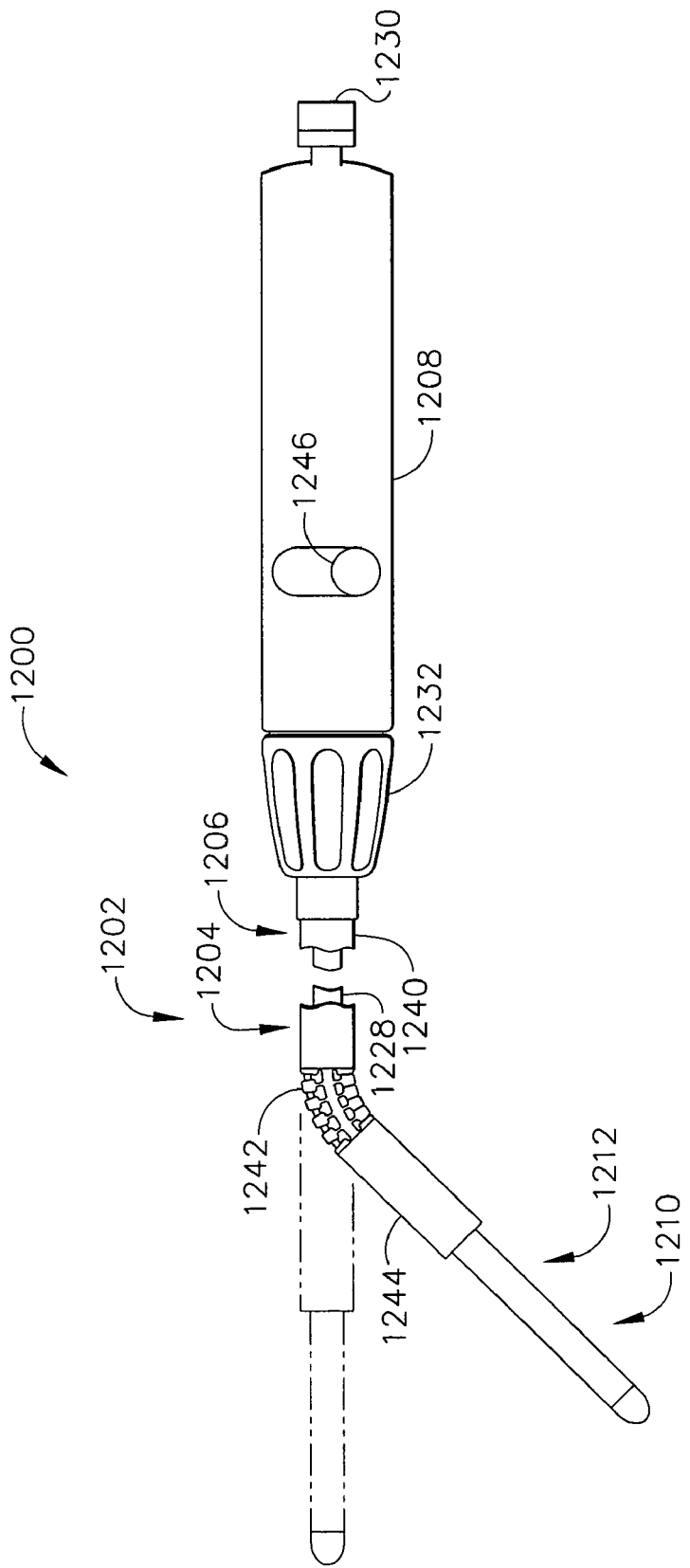
FIG. 1A is a top view of the surgical instrument of FIG. 1 articulating to the left.

The articulating frame assembly 1204 includes a proximal frame ground 1240 proximally and rotatably attached to the handle 1208 and that is distally attached to an articulating frame ground 1242 that in turn is attached to a distal frame ground 1244 that supports the end effector 1210. An articulation control 1246 on the handle 1208 advantageously allows the selection of articulating the articulating frame ground 1242 by activating appropriate electrical signals thereto, such as depicted in FIG. 1A when a leftward articulation has been selected by articulation control 1246. It should be appreciated that the articulation control 1246 may advantageously include manual and/or automatic disengagement of an articulation lock for the articulating frame ground 1242.

Handle.

In FIG. 1, the staple applying assembly 12 accomplishes the functions of clamping onto tissue, driving staples and severing tissue by two distinct motions transferred longitudinally down the shaft 1206 over a shaft frame (not shown in FIG. 1 but described below regarding FIG. 7). This shaft frame assembly is proximally attached to the handle 14 and coupled for rotation with the rotation knob 30. An illustrative multi-stroke handle 14 for the surgical stapling and severing instrument 10 of FIG. 1 is described in greater detail in the co-pending and co-owned U.S. patent applications entitled "SURGICAL STAPLING INSTRUMENT INCORPORATING A MULTISTROKE FIRING POSITION INDICATOR AND RETRACTION MECHANISM" to Swayze and Shelton, Ser. No. 10/674,026, and entitled "SURGICAL STAPLING INSTRUMENT INCORPORATING A MULTI-STROKE FIRING MECHANISM WITH AUTOMATIC END OF FIRING TRAVEL RETRACTION", Ser. No. 11/052,632, filed on Feb. 7, 2005 to Kevin Doll, Jeffrey S. Swayze, Frederick E. Shelton IV, Douglas Hoffman, and Michael Setser, the disclosures of which are hereby incorporated by reference in their entirety, with additional features and variation as described herein.

While a multi-stroke handle 14 advantageously supports applications with high firing forces over a long distance, applications consistent with the present invention may incorporate a single firing stroke, such as described in co-pending and commonly owned U.S. patent application "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgarn, Ser. No. 10/441,632, the disclosure of which is hereby incorporated by reference in its entirety.

Electroactive Polymers.

Electroactive polymers (EAPs) are a set of conductive doped polymers that change shape when an electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential range from 1V to 4 kV depends on the polymer and ionic fluid used. Some of the EAPs contract when voltage is applied and some expand. The EAPs may be paired to mechanical means such as springs or flexible plates to change the effect that is caused when the voltage is applied.

There are two basic types and multiple configurations of each type. The two basic types are a fiber bundle and a laminate version. The fiber bundle consists of fibers around 30-50 microns. These fibers may be woven into a bundle much like textiles and are often called EAP yarn because of this. This type of EAP contracts when voltage is applied. The electrodes are usually a central wire core and a conductive outer sheath, which also serve to contain the ionic fluid that surrounds the fiber bundles. An example of a commercially available fiber EAP material is manufactured by Santa Fe Science and Technology, is sold as PANION™ fiber and is described in U.S. Pat. No. 6,667,825, which is hereby incorporated by reference in its entirety.

The other type is a laminate structure. It consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is manufactured by Artificial Muscle Inc, a division of SRI Laboratories. Plate EAP material is also available from EAMEX of Japan and referred to as thin film EAP.

It should be noted that EAPs do not change volume when energized, they merely expand or contract in one direction while doing the opposite in the transverse direction. The laminate version may be used in its basic form by containing one side against a rigid structure and using the other much like a piston. It may also be adhered to either side of a flexible plate. When one side of the flexible plate EAP is energized, it would expand, flexing the plate in the opposite direction. This allows the plate to be flexed in either direction, depending on which side is energized.

An EAP actuator usually is made up of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration, when the electrical filed is applied to the electrodes, the strands of EAP would shorten. This configuration of EAP actuator is called a fiber EAP actuator. Likewise, the laminate configuration may be placed in numerous layers on either side of a flexible plate or merely in layers on itself to increase its capabilities. Typical fiber structures have an effective strain of 2-4% where the typical laminate version achieves 20-30% utilizing much higher voltages.

Figure 2:
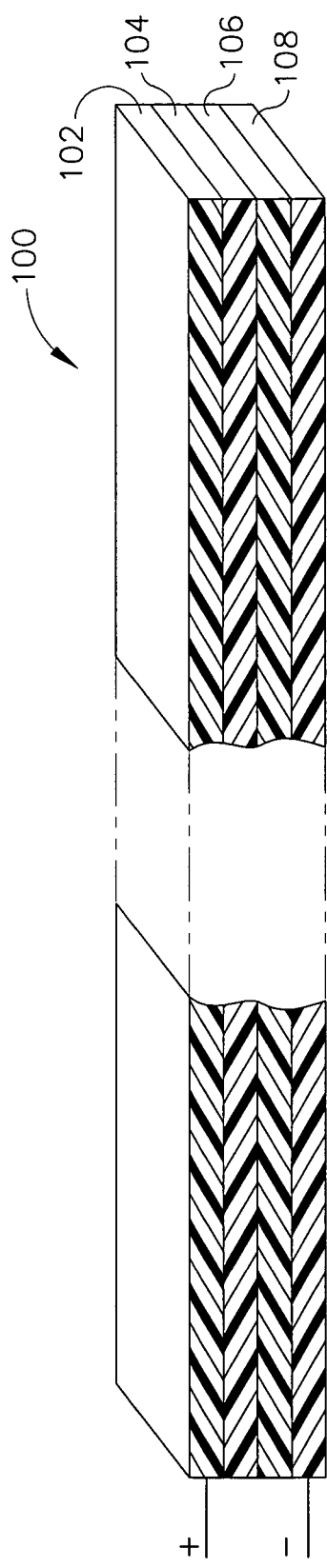
FIG. 2 is a perspective view of a laminate Electroactive Polymer (EAP) composite.
Figure 3:
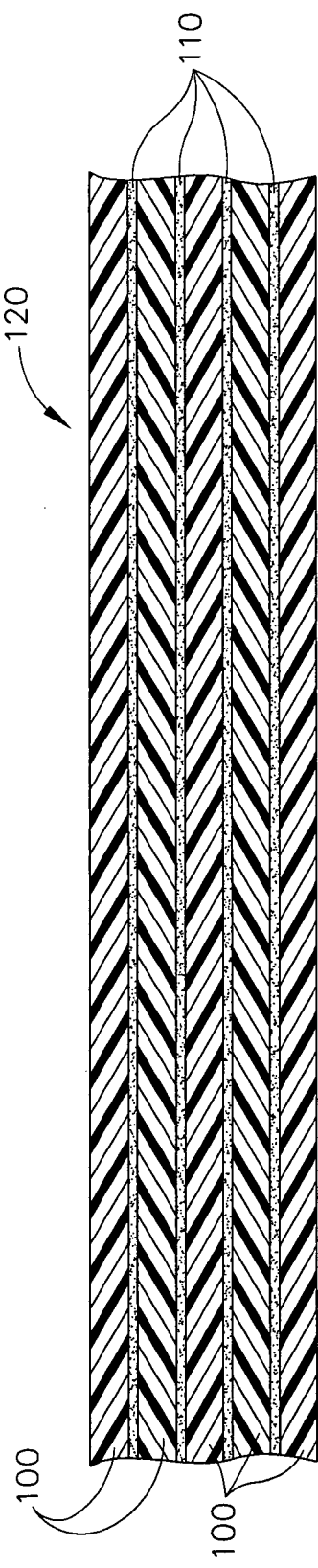
FIG. 3 is a perspective view of an EAP plate actuator formed from a stack formed from an adhesively affixed plurality of laminate EAP composites of FIG. 2.

In FIG. 2, a laminate EAP composite 100 is depicted as being formed from a positive plate electrode layer 1302 attached to an EAP layer 104, which in turn is attached to an ionic cell layer 106, which in turn is attached to a negative plate electrode layer 108. In FIG. 3, a plurality of five laminate EAP composites 100 are affixed in a stack by adhesive layers 110 therebetween to form an EAP plate actuator 120. It should be appreciated that opposing EAP actuators 120 may be formed that can be selected to bend in either direction.

In FIGS. 4-5, a contracting EAP fiber actuator 140 includes a longitudinal platinum cathode wire 142 that passes through an insulative polymer proximal end cap 144 through an elongate cylindrical cavity 146 formed within a plastic cylinder wall 148 that is conductively doped to serve as a positive anode. A distal end of the platinum cathode wire 142 is embedded into an insulative polymer distal end cap 150. A plurality of contracting polymer fibers 152 are arranged parallel with and surrounding the cathode wire 142 and have their ends embedded into respective end caps 144, 150. The plastic cylinder wall 148 is peripherally attached around respective end caps 144, 150 to enclose the cylindrical cavity 146 to seal in ionic fluid or gel 154 that fills the space between contracting polymer fibers 152 and cathode wire 142. When a voltage is applied across the plastic cylinder wall (anode) 148 and cathode wire 142, ionic fluid enters the contracting polymer fibers 152, causing their outer diameter to swell with a corresponding contraction in length, thereby drawing the end caps 144, 150 toward one another.

EAP Actuated Articulation Joint.

Figure 6:
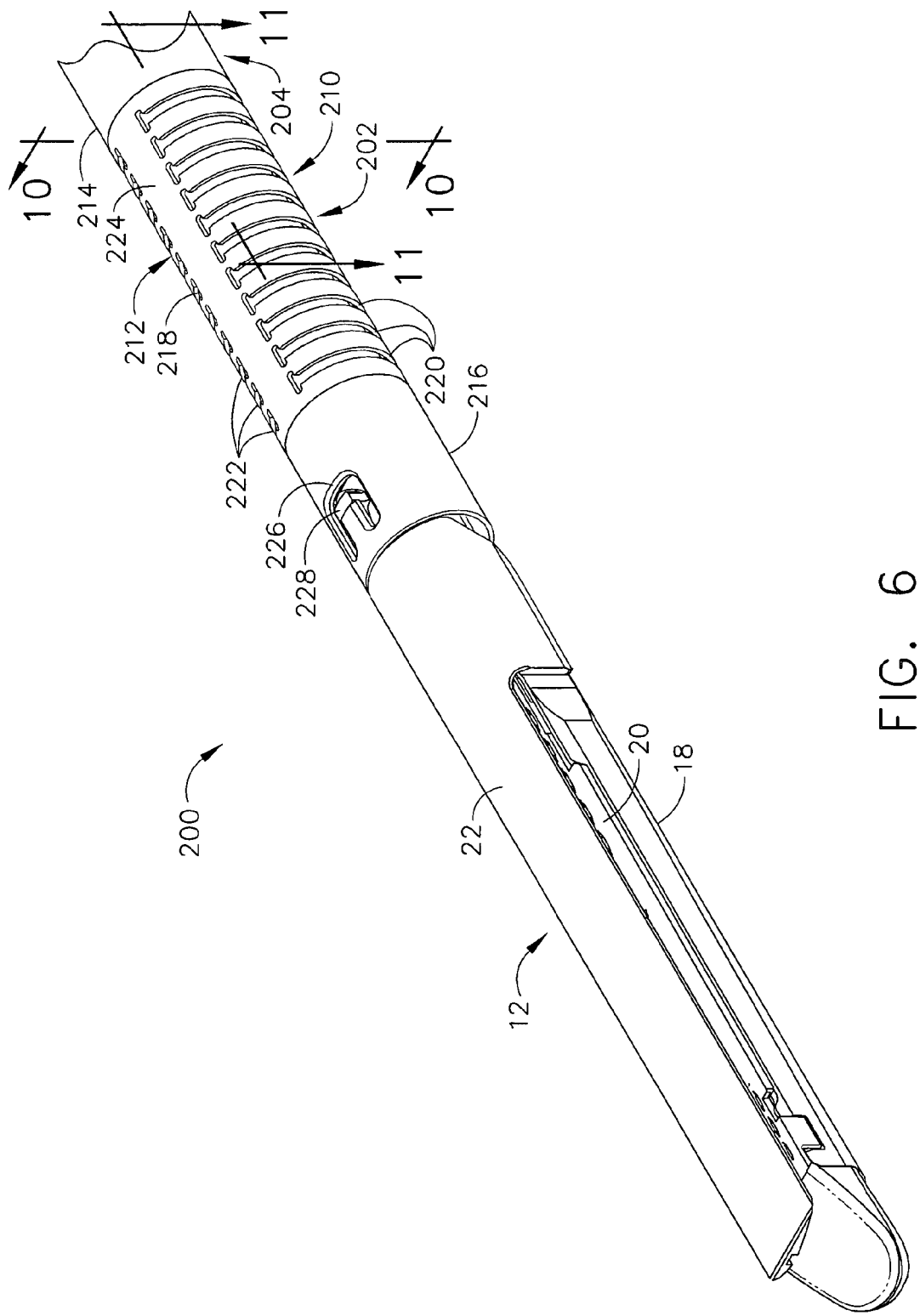
FIG. 6 is a front right perspective view of an EAP actuated articulation joint for the surgical instrument of FIG. 1 with a laterally flexible closure sleeve assembly and a flexible neck frame assembly and a closed staple applying assembly.
Figure 7:
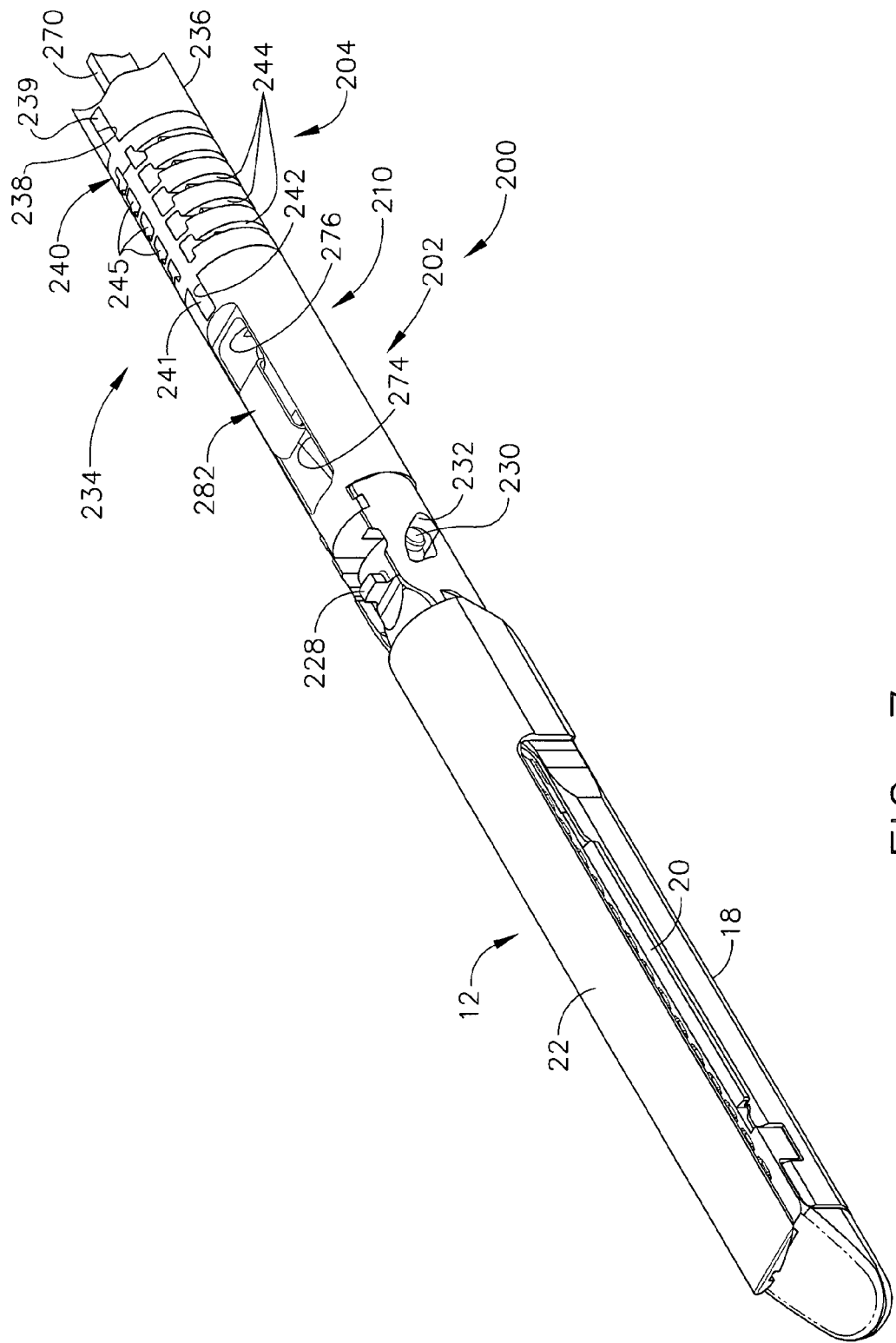
FIG. 7 is a front right perspective view of the EAP actuated articulation joint and closed staple applying assembly of FIG. 6 with a flexible closure sleeve assembly removed and a flexible neck frame assembly partially exploded.

In FIGS. 6-7, a surgical severing and stapling instrument 200 includes an EAP actuated articulation joint 202 that is formed in its elongate shaft 204 proximate to the end effector, which is illustrated by the surgical stapling and severing assembly 12 that advantageously responds to separate closure and firing motions that are transferred longitudinally by the elongate shaft 204. The EAP actuated articulation joint 202 advantageously adds the desirable clinical flexibility of articulating the staple applying assembly 12.

Figure 8:
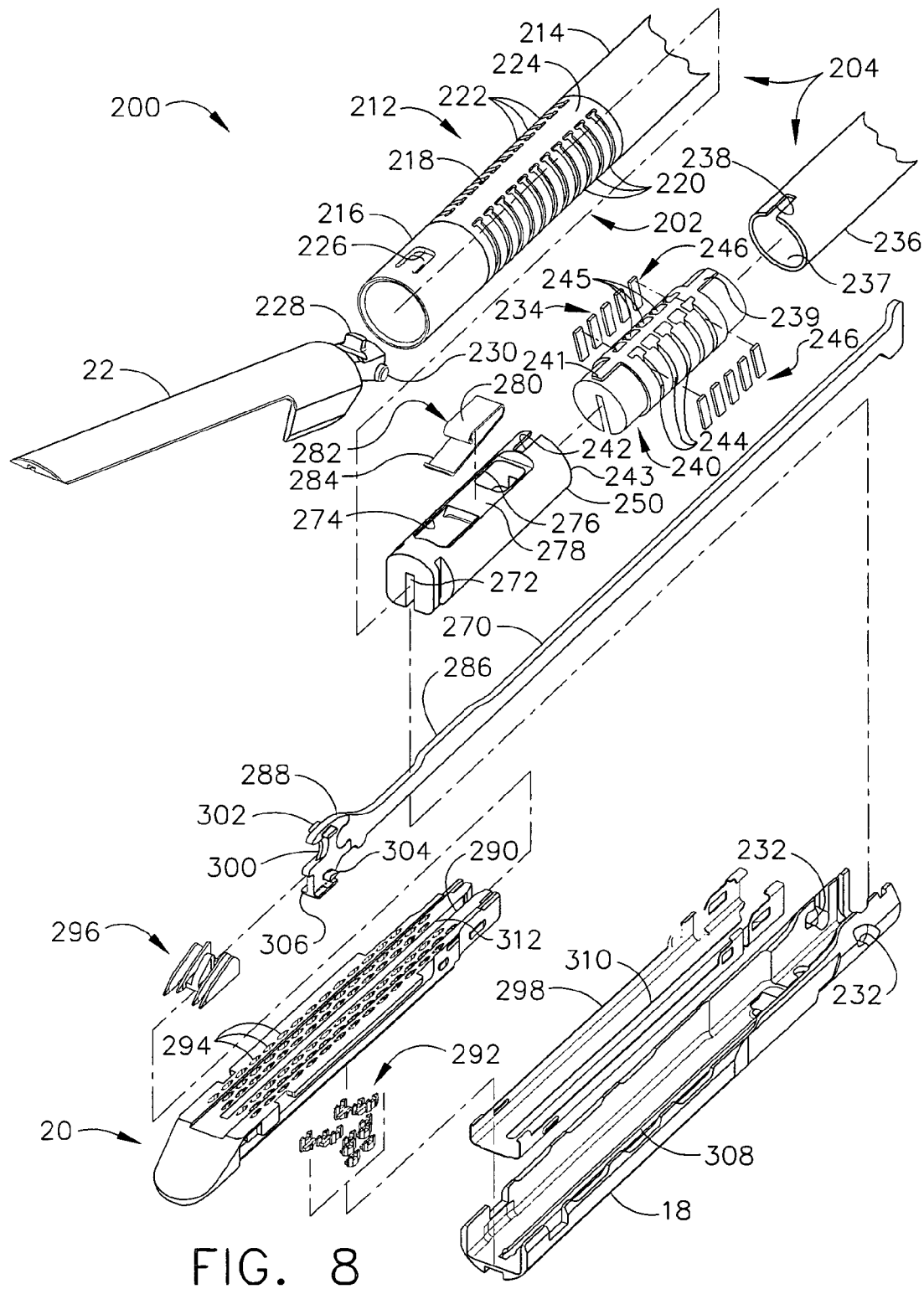
FIG. 8 is a front right exploded perspective view of the EAP actuated articulation joint and staple applying assembly of FIG. 6.
Figure 9:
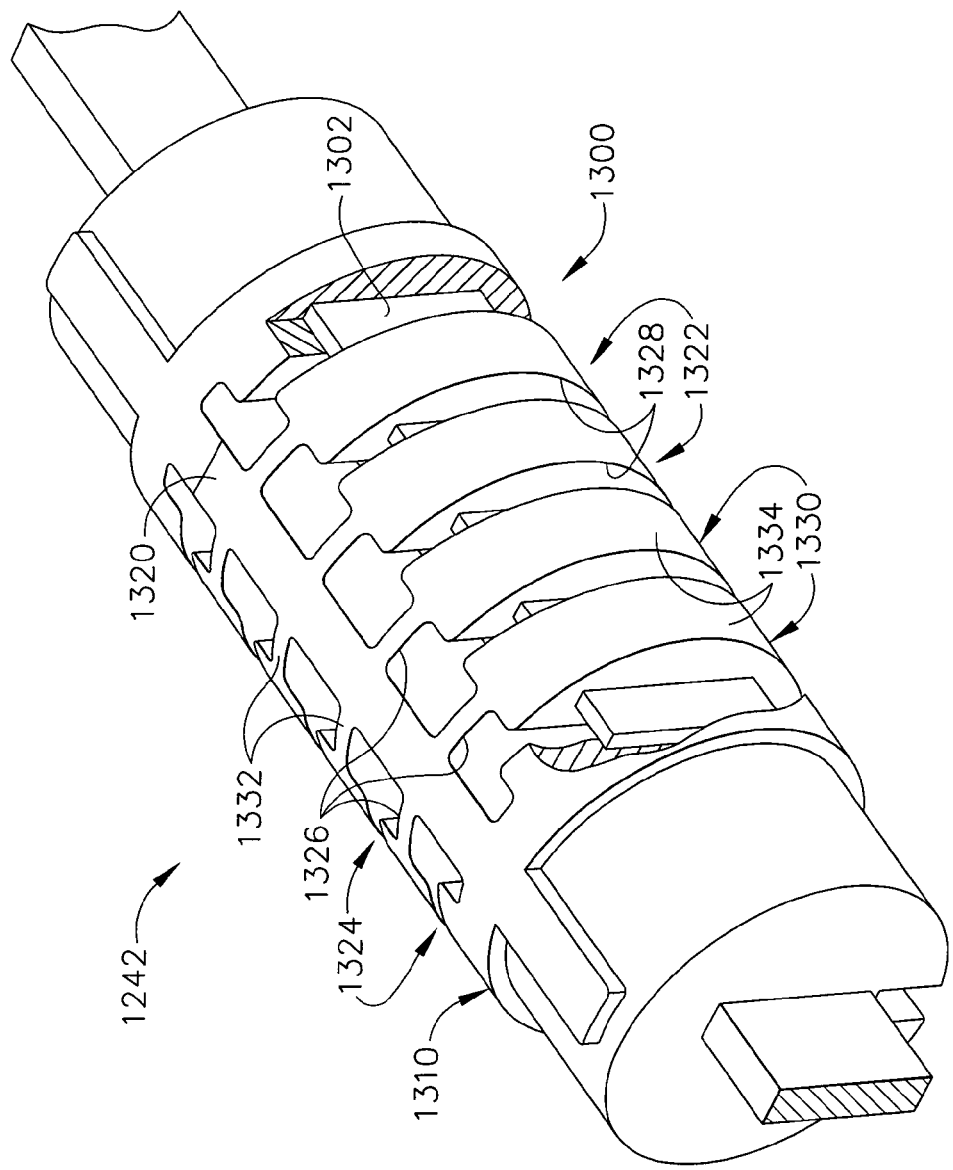
FIG. 9 is a front right perspective view of the articulating frame ground of FIG. 1 that incorporates EAP plate actuators and locking strips.

In the illustrative version of FIGS. 6-8, the EAP actuated articulation joint 202 is more particularly a flexible closure and pivoting frame articulation joint 210, which in FIG. 6 is shown to include a flexible closure sleeve assembly 212 having a proximal closure tube 214 and distal closure ring 216 connected by a flexible closure tube 218. Left and right longitudinal rows of vertical slits 220, 222 formed in the flexible closure tube 218 allow flexing to the right or to the left for articulation, yet an uninterrupted top longitudinal band 224 and bottom longitudinal band (not shown) transfer a longitudinal closure motion regardless of an amount of such flexing. In particular, a top portion of the distal closure ring 216 includes a horseshoe aperture 226 that engages an anvil closure feature 228 of the anvil 22. In FIGS. 7-8, the anvil 22 includes laterally projecting pivot pins 230 at its proximal end that pivotally engage pivot apertures 232 formed near the proximal end of the elongate channel 18. The slightly more distal anvil closure feature 228 thus imparts a closing motion when the flexible closure sleeve assembly 212 moves distally and imparts an opening motion when moving proximally. The flexible closure tube 218 may bend along the length of the left and right longitudinal rows of vertical slits 220, 222, thus accommodating an encompassed laterally flexible frame assembly 234 of the flexible closure and pivoting frame articulation joint 210 when articulated.

In FIGS. 6-8, the laterally flexible frame assembly 234 includes a proximal frame ground 236 that includes a distally open cylindrical end 237 with top slot 238 that engages a top key tab 239 on a proximal end of a flexible frame member 240. A distal end of the flexible frame member 240 in turn has a distally presented top key tab 241 that is received within a top slot 242 in a proximally open cylindrical end 243 of a distal frame ground 250. Left and right vertical slots 244, 245 in the flexible frame member 240 allow for EAP actuators 245 that are inserted into these slots 244, 245 to assert an articulation motion to the flexible frame assembly 234.

In FIG. 8, an implement portion 260 of the surgical instrument 200, formed by the elongate shaft 16 and staple applying assembly 12, further includes a firing bar 270 that longitudinally translates through the proximal frame ground 218, through the flexible closure and pivoting frame articulation joint 210, and through a firing slot 272 in the distal frame ground 250 into the staple applying assembly 12. Distal and proximal square apertures 274, 276, formed on top of the distal frame ground 250, define a clip bar 278 therebetween that receives a top arm 280 of a clip spring 282 whose lower, distally extended arm 284 asserts a downward pressure on a raised portion 286 along an upper portion of the firing bar 270 corresponding to the empty/missing cartridge lockout portion of firing travel.

With particular reference to FIG. 8, a distally projecting end of the firing bar 270 is attached to an E-beam 288 that assists in spacing the anvil 22 from the staple cartridge 20, severs tissue, and actuates the staple cartridge 20. The staple cartridge 20 includes a molded cartridge body 290 that holds a plurality of staples resting upon staple drivers 292 within respective upwardly open staple apertures 294. A wedge sled 296 is driven distally by the E-beam 288, sliding upon a cartridge tray 298 that holds together the various components of the replaceable staple cartridge 20. The wedge sled 296 upwardly cams the staple drivers 292 to force out the staples into deforming contact with the anvil 22 while a cutting surface 300 of the E-beam 288 severs clamped tissue. It should be appreciated that upper pins 302 of the E-beam 288 engage the anvil 22 during firing while middle pins 304 and a bottom foot 306 engage the respective top and bottom surfaces of a longitudinal slot 308 formed in the elongate channel 18, with a corresponding longitudinal opening 310 in the cartridge tray 298 and a rearwardly open vertical slot 312 in the cartridge body 290. Thereafter, the firing bar 270 is retracted proximally, retracting as well the E-beam 288, allowing the anvil 22 to be opened to release the two stapled and severed tissue portions (not shown).

The staple applying assembly 12 is described in greater detail in co-pending and commonly-owned U.S. patent application Ser. No. 10/955,042, "ARTICULATING SURGICAL STAPLING INSTRUMENT INCORPORATING A TWO-PIECE E-BEAM FIRING MECHANISM" to Frederick E. Shelton IV, et al., filed 30 Sep. 2004, the disclosure of which is hereby incorporated by reference in its entirety.

Figure 10:
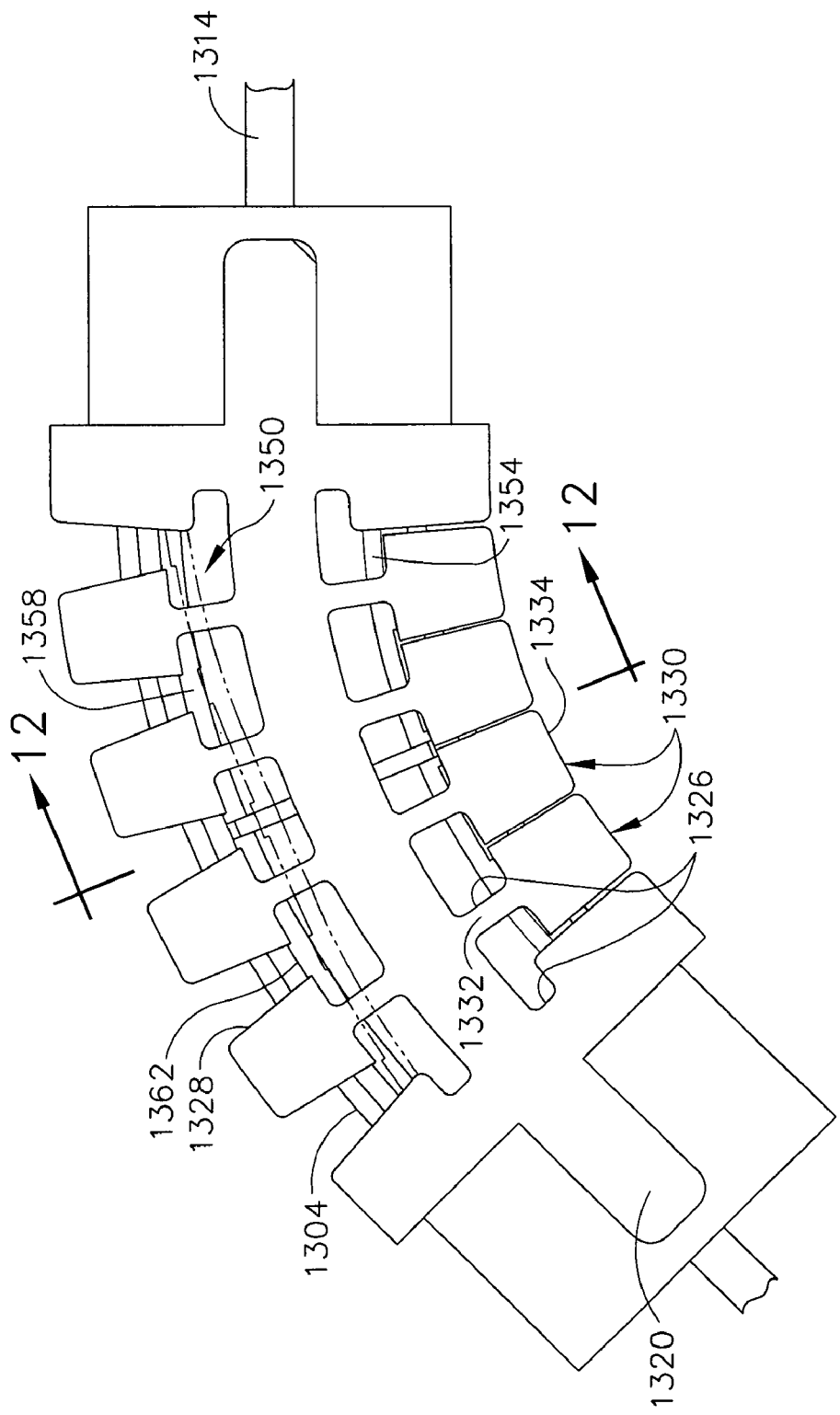
FIG. 10 is a top view of the articulating frame ground of FIG. 1A in a left articulated state with a left EAP locking strip shown in phantom in an unlocked actuated state and a locked relaxed state.
Figure 11:
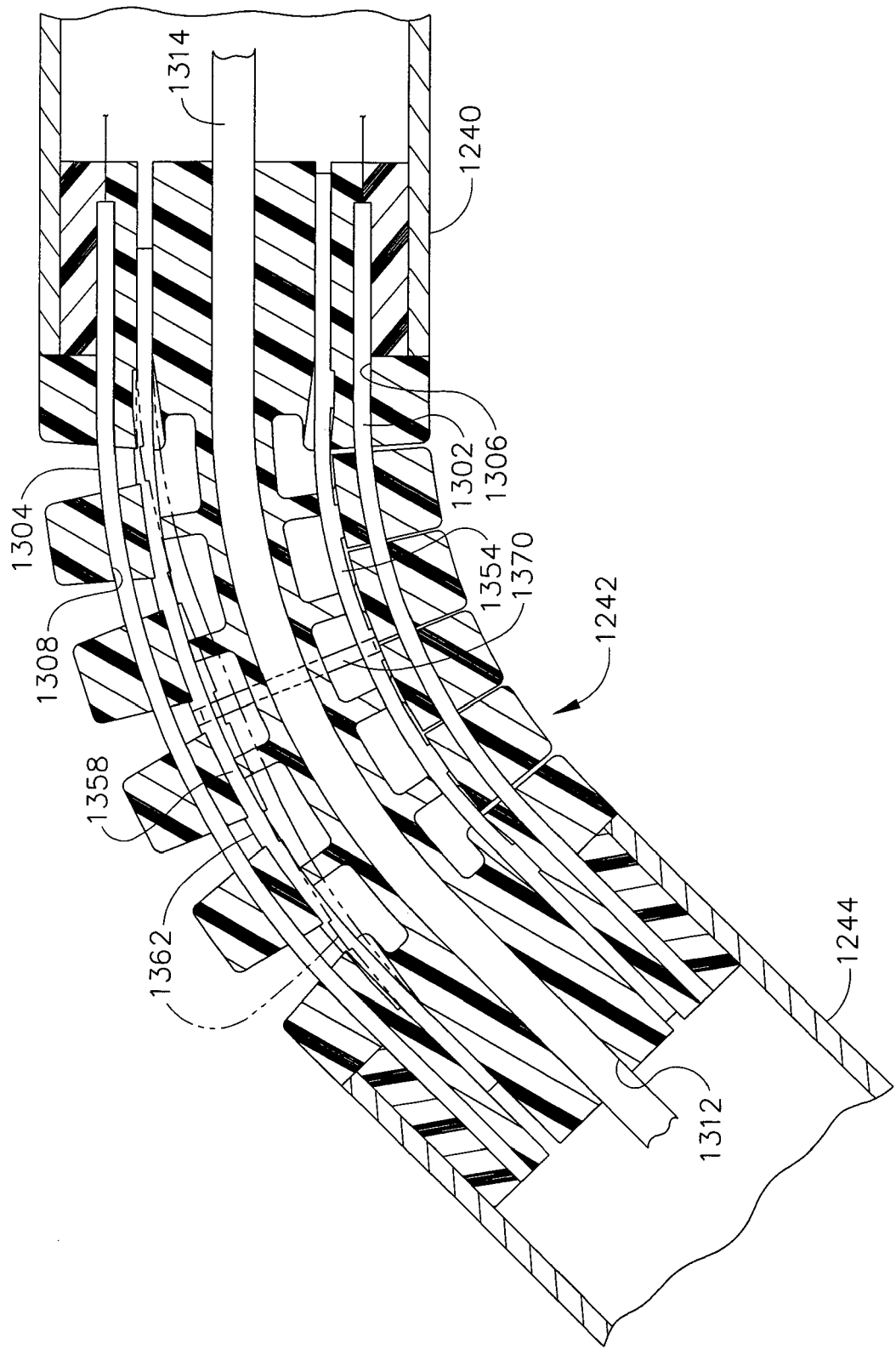
FIG. 11 is a top view of the articulating frame ground of FIG. 1A in a left articulated state taken in cross section through the EAP plate actuators and EAP locking strips.
Figure 12:
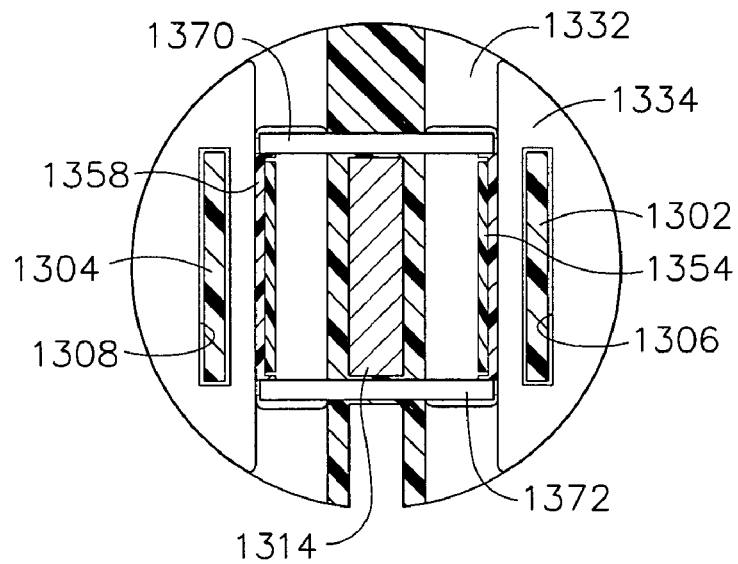
FIG. 12 is a front view in elevation of the articulating frame ground of FIG. 10 taken in cross section through lines 12-12 through the lateral guide pins.

As an alternative to the flexible frame assembly 234, in FIGS. 9-12, the articulating frame ground 1242 incorporates an EAP actuating system 1300 that uses left and right EAP plate actuators 1302, 1304 that pass through respective left and rectangular actuator recesses 1306, 1308 (FIGS. 11-12)

in each lateral side of a generally cylindrical resilient frame body 1310. A rectangular knife slot 1312 is formed in the resilient frame body 1310 aligned between the left and right rectangular actuator recesses 1306, 1308 for guiding a firing bar 1314 that is a distal portion of the firing member 1228.

Continuous top and bottom longitudinal bands 1320 (FIGS. 9-10) of the resilient frame body 1310 maintain a longitudinal amount of travel for the firing bar 1314 when the articulating frame ground 1242 is either straight or articulated. To advantageously allow forming of the resilient frame body 1310 from a homogenous material that does not significantly compress along its longitudinal axis, left and right pluralities of longitudinally aligned vertical recesses 1322, 1324 intersect respectively with the left and right EAP actuator recesses 1306, 1308. Each vertical recess 1322, 1324 includes a rectangular through hole 1326 that passes from top to bottom through the resilient frame body 1310 parallel with and laterally offset from both the rectangular knife slot 1312 and the appropriate one of either the left or right rectangular actuator recess 1306, 1308. Each rectangular through hole 1326 communicates laterally with a narrowed lateral gap 1328. Adjacent vertical recesses 1322, 1324 define therebetween a rib 1330 that has a narrow inner wall 1332, which allows lateral bending of the continuous top and bottom longitudinal bands 1320, and a thicker curved outer slice 1334 that supports the respective one of the EAP plate actuators 1302, 1304 and limits the amount of articulation that may be achieved in that direction before the narrowed lateral gaps 1328 collapse fully as one or both EAP plate actuators 1302, 1304 are activated to bend in a selected direction. In FIG. 10, for instance, the left EAP plate actuator 1302 is activated to actuate to the left with the right EAP plate actuator 1304 stretching in response. It should be appreciated that the left and right EAP plate actuators 1302, 1304 may alternatively contract or expand when electrically activated to create a pull or a push respectively within the left and right rectangular actuator recesses 1306, 1308.

In FIGS. 11-12, the articulating frame ground 1242 advantageously includes an EAP articulation locking mechanism 1350 that selectively holds the resilient frame body 1310 in an articulated left or an articulated right condition. To that end, a left locking passage 1352 is defined passing through the left plurality of rectangular through holes 1326 proximate to their leftmost outer portion, allowing a left ridged EAP locking strip 1354 to pass therethrough. Similarly, a right locking passage 1356 is defined passing through the right plurality of rectangular through holes 1326 proximate to their rightmost outer portion, allowing a right ridged EAP locking strip 1358. Along their respective outermost surface 1360 of both the left and right ridged EAP locking strips 1354, 1358, a plurality of longitudinally spaced vertical blocking ridges 1362 are longitudinally spaced and sized to define, in conjunction with the geometry of the ribs 1330, to lock at a desired articulation amount. In particular, when the flexible frame ground 1242 articulates toward the opposite side of a respective ridged EAP locking strip 1354, 1358, the ribs 1330 on that side arc away from one another, as depicted in FIG. 11 in articulating to the left. Once the ribs 1330 have reached a spacing sufficient for locking (i.e., wider than the longitudinal width of the vertical blocking ridges 1362), the right ridged EAP locking strip 1358 is biased outwardly to snap its ridges 1362 between adjacent thickened curved outer slices 1334 of adjacent ribs 1330. Activating the right ridged EAP locking strip 1358 causes contraction that unlocks the right ridged EAP locking strip 1358. In FIG. 12, lateral upper and lower guide pins 1370, 1372 pass above and below the rectangular knife slot 1312 to preserve lateral alignment.

Figure 13:
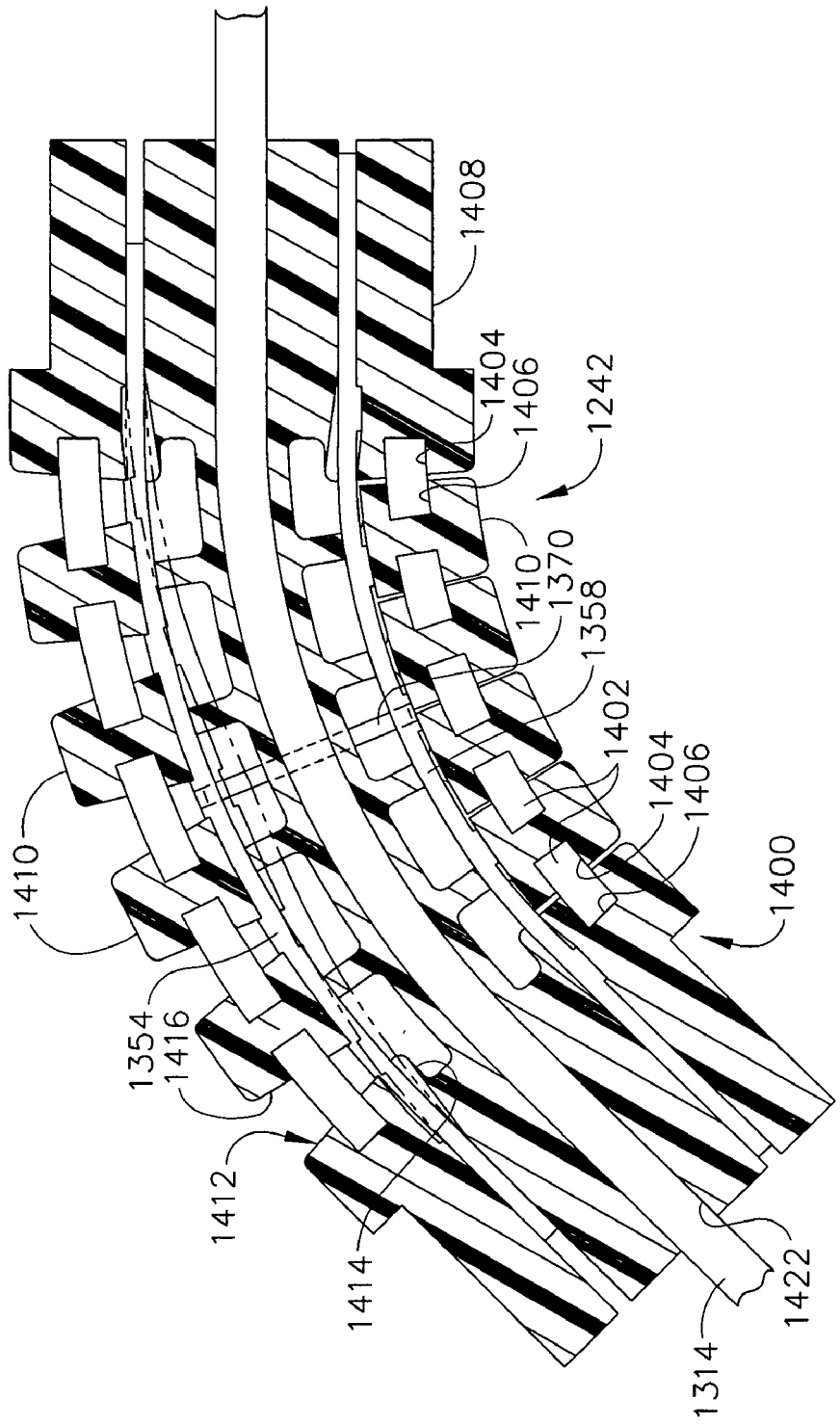
FIG. 13 is a top view of an alternate articulating frame ground for the surgical instrument of FIG. 1 taken in cross section through a plurality of EAP rib spreader actuators.

In FIG. 13, the articulating frame ground 1242 incorporates an EAP actuating system 1400 that uses a left plurality left and right EAP rib spreader plate actuator 1402 that resides between an opposing pair of distally and proximally open rectangular recesses of a resilient frame body 1408. Each opposing pair of distally and proximally open rectangular actuator recesses 1404, 1406 respectively are formed in an adjacent pair (proximal/distal) of laterally defined ribs 1410. Each rib 1410 includes a vertical slot 1412 that is open outwardly laterally along its height with a wider rectangular through hole 1414 more inwardly positioned that narrows into an outer vertical slot 1416. Each rib 1410 thus includes a thin inner wall 1418 that connects to upper and lower longitudinal continuous bands 1420. A rectangular knife slot 1422 is formed laterally along the longitudinal centerline. Left and right ridged EAP locking strips 1354, 1358 as described above advantageously relax to an expanded curved shape on the expanded side of the articulating frame ground 1242 to lock, with longitudinal alignment maintained by lateral guide pins 1370.

Figure 15:
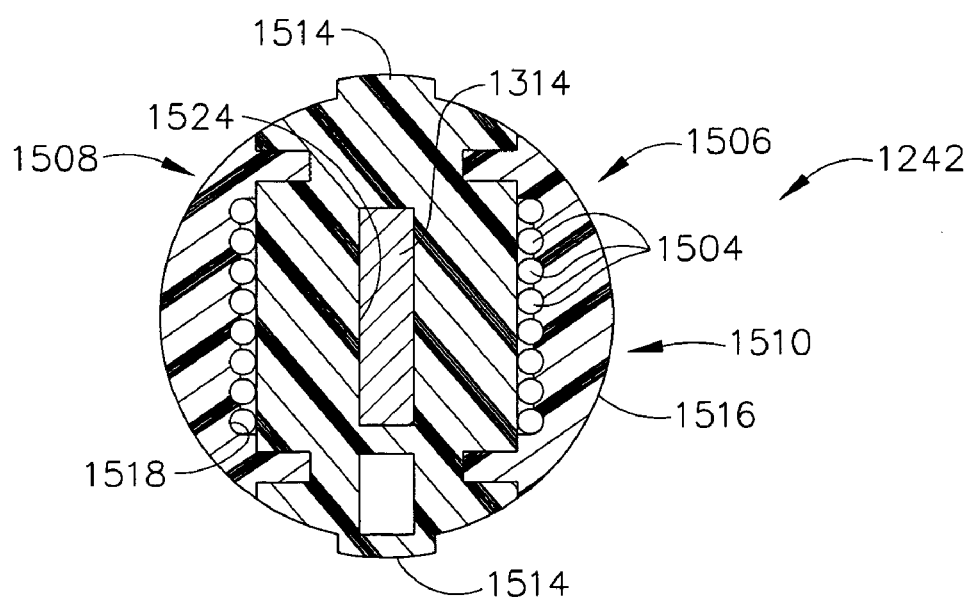
FIG. 15 is a front view in elevation of the additional alternative articulating frame ground of FIG. 14 taken in cross section along lines 15-15.
Figure 14:
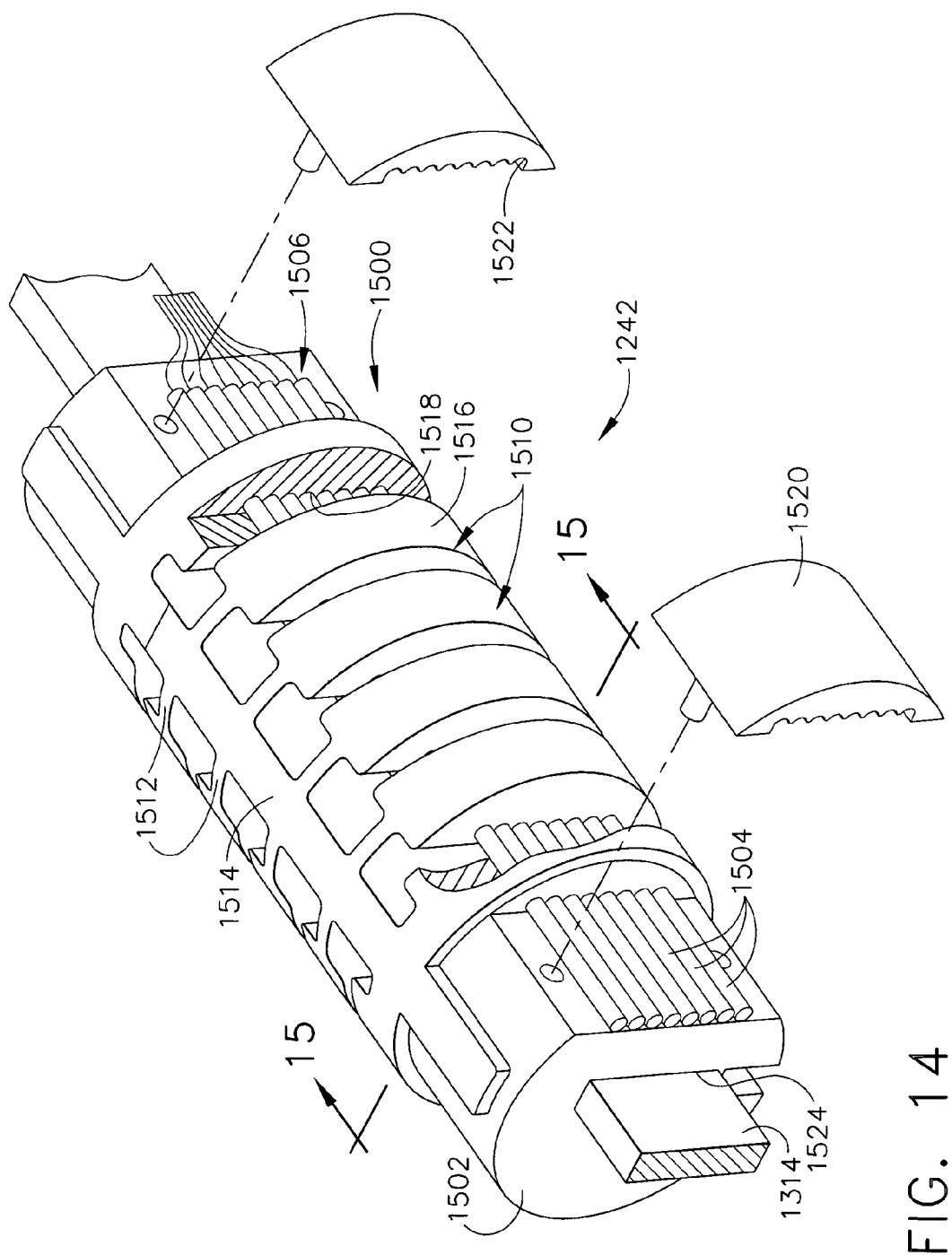
FIG. 14 is a right perspective partially exploded view of an additional alternative articulating frame ground having a plurality of EAP fiber actuators for the surgical instrument of FIG. 1.

In FIGS. 14-15, the articulating frame ground 1242 incorporates a further alternative EAP actuating system 1500 into a resilient frame body 1502 that includes longitudinally aligned EAP fiber actuators 1504 arranged in left and right vertical stacks 1506, 1508 that pass through a respectively left and right plurality of lateral ribs 1510 each having a thin inner vertical wall 1512 that connects to continuous longitudinal top and bottom bands 1514 to facilitate lateral bending thereof. Each rib 1510 widens laterally to a thick outer slice 1516 that is dimensioned for the limitation of articulation to that side. Each thick outer slice 1516 includes vertical aligned longitudinal through holes 1518 for allowing the EAP fiber actuators 1504 to pass through. Distal and proximal lateral covers 1520, 1522 longitudinally flank the ribs 1510 to cover respective termination ends of the EAP fiber actuators 1504. A laterally centered knife slot 1524 is formed in the resilient frame body 1502 for the firing bar 1314. Contracting a selected vertical stack 1506, 1508 of EAP fiber actuators 1504 causes articulation to that side with the nonactuated vertical stack 1506, 1508 passively elongating in response thereto.

EAP Support Plates For Firing Bar.

Figure 16:
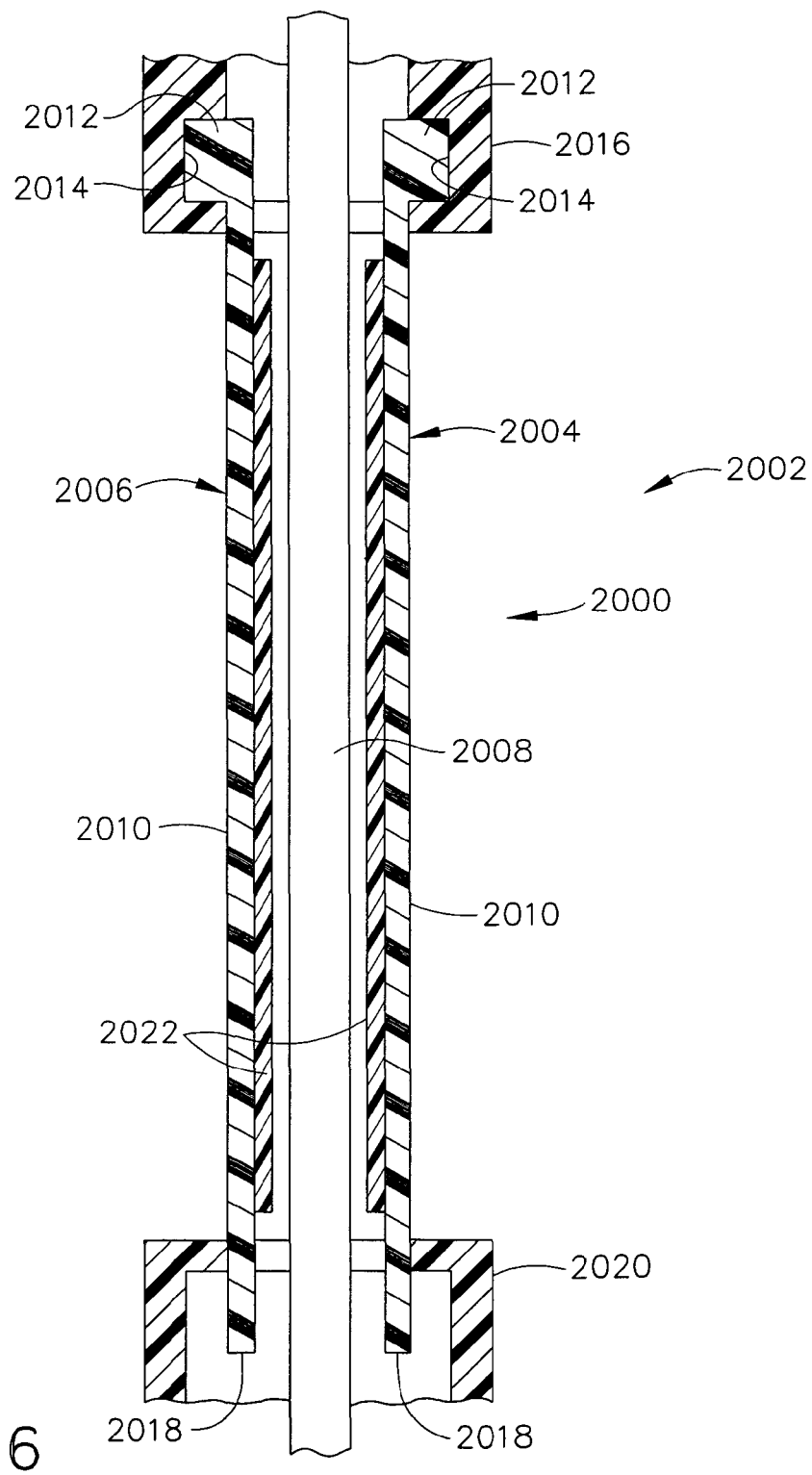
FIG. 16 is a top view taken in longitudinal cross section of a firing bar passing through an articulation joint of a surgical instrument with the firing bar advantageously laterally guided by support plates of inwardly actuated EAP plate actuators with one sliding end.

In FIG. 16, an articulation joint 2000 for a surgical instrument 2002 includes a pair of EAP support plates 2004, 2006 that laterally support a firing bar 2008 to minimize binding and buckling when articulated. Each support plate 2004, 2006 includes a structural member 2010 (e.g., rigid polymer, metal) that includes a laterally widened end 2012 that is captured within a correspondingly sized recess 2014 in a first frame ground 2016 and a straight end 2018 that is slidingly received within a second frame ground 2020. A longitudinally expansive EAP laminate 2022 covers an internal surface of each support plate 2004, 2006.

Figure 17:
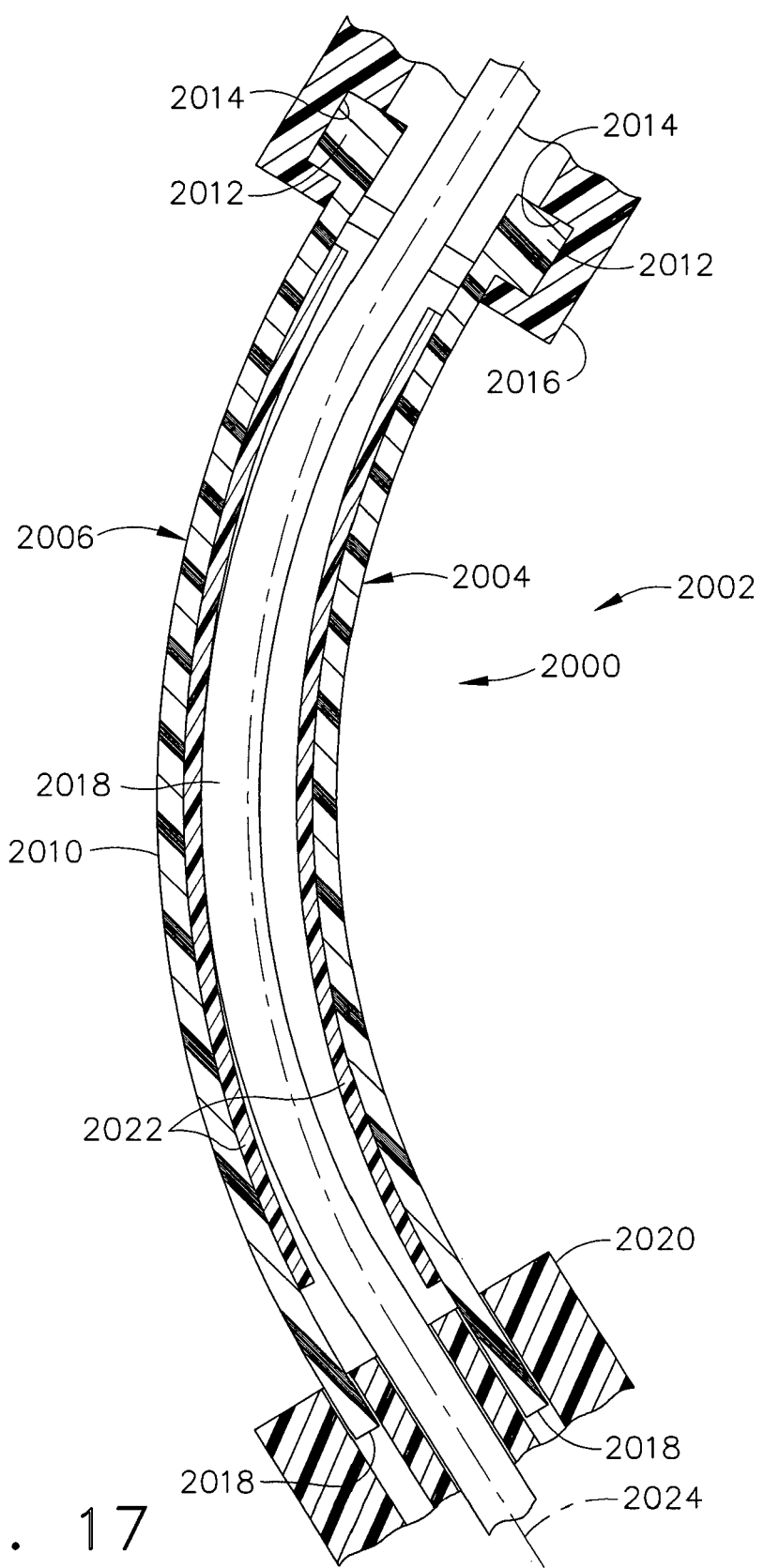
FIG. 17 is a top view taken in longitudinal cross section of the firing bar passing through an articulated articulation joint of the surgical instrument of FIG. 16.

In FIG. 17, the articulation joint 2000 is articulated to one lateral side, causing the firing bar 2008 to overshoot an articulated longitudinal axis 2024 and come into contact with support plate 2006. Lateral support therefrom prevents a blow out of the firing bar 2008 out of the articulation joint 2000 and/or allows fabrication of a more flexible firing bar 2008 with thus reduced force to articulate. In addition, the EAP laminates 2022 on each support plate 2004, 2006 are activated as necessary to control the amount of curvature of both to preserve a desired spacing therebetween for the firing bar 2008. The straight ends 2018 slide in the second frame ground portion 2020 to accommodate the reduced travel required of the inner support plate 2004 as compared to the outer support plate

2006. The EAP laminate 2022 may further provide cushioning and low surface friction characteristics that assist in laterally guiding the firing bar 2008.

Figure 18:
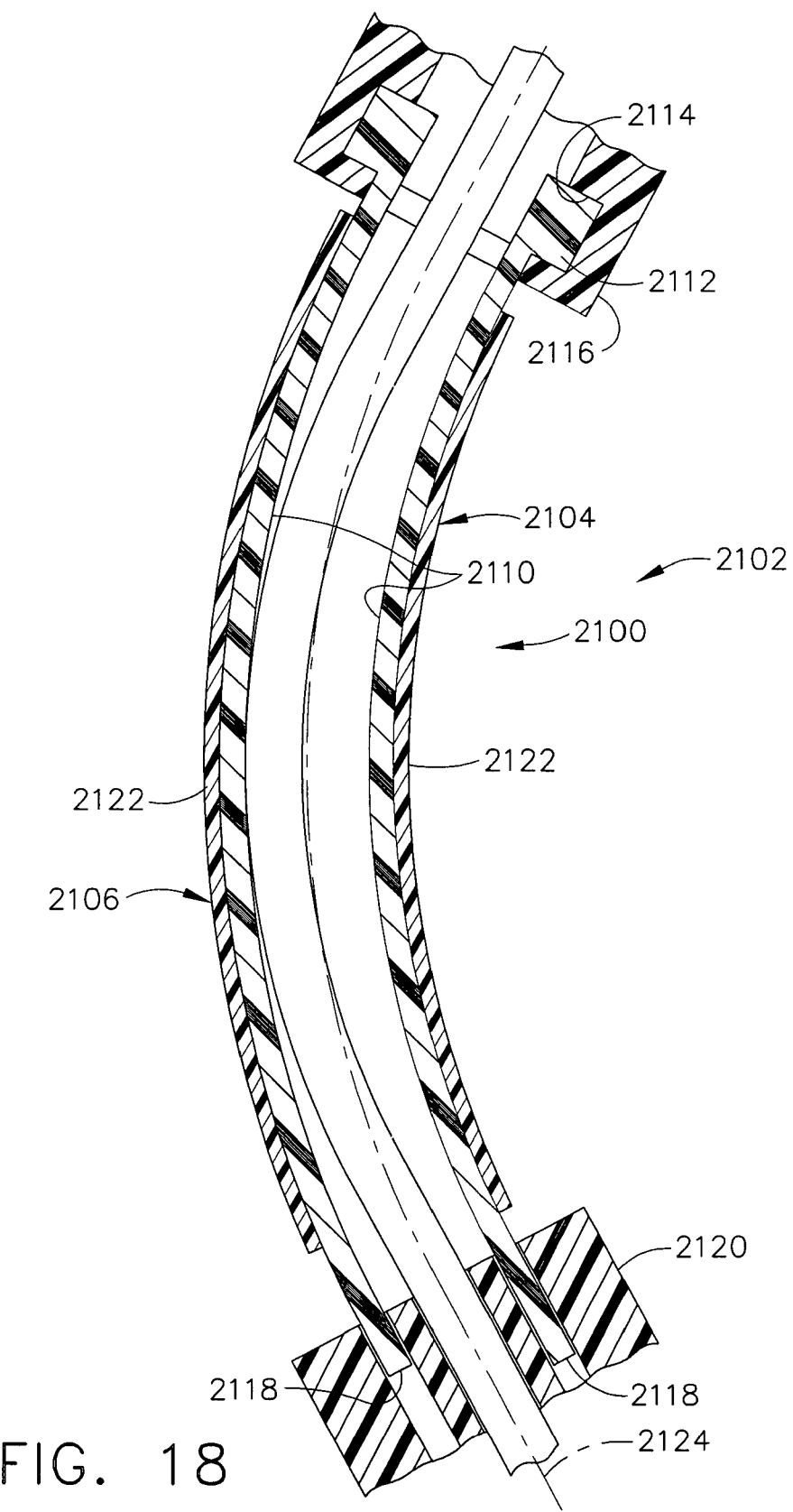
FIG. 18 is a top view taken in longitudinal cross section of a firing bar passing through an articulated articulation joint of a surgical instrument with the firing bar advantageously laterally guided by support plates of outwardly actuated EAP plate actuators with one sliding end.

In FIG. 18, an alternative articulation joint 2100 for a surgical instrument 2102 includes a pair of EAP support plates 2104, 2106 that laterally support a firing bar 2108 to minimize binding and buckling when articulated. Each support plate 2104, 2106 includes a structural member 2110 (e.g., rigid polymer, metal) that includes a laterally widened end 2112 that is captured within a correspondingly sized recess 2114 in a first frame ground 2116 and a straight end 2118 that is slidingly received within a second frame ground 2120. A longitudinally expansive EAP laminate 2122 covers an outer surface of each support plate 2104, 2106. The articulation joint 2100 is articulated to one lateral side, causing the firing bar 2108 to overshoot an articulated longitudinal axis 2124 and come into contact with support plate 2106. Lateral support therefrom prevents a blow out of the firing bar 2108 out of the articulation joint 2100 and/or allows fabrication of a more flexible firing bar 2108 with thus reduced force to articulate. In addition, the EAP laminates 2122 on each support plate 2104, 2106 are activated as necessary to control the amount of curvature of both to preserve a desired spacing therebetween for the firing bar 2108. The straight ends 2118 slide in the second frame ground portion 2120 to accommodate the reduced travel required of the inner support plate 2104 as compared to the outer support plate 2106. Placement of the EAP laminates 2122 away from contact from the firing bar 2108 may have advantages such as reducing wear to the EAP laminates 2122.

Figure 19:
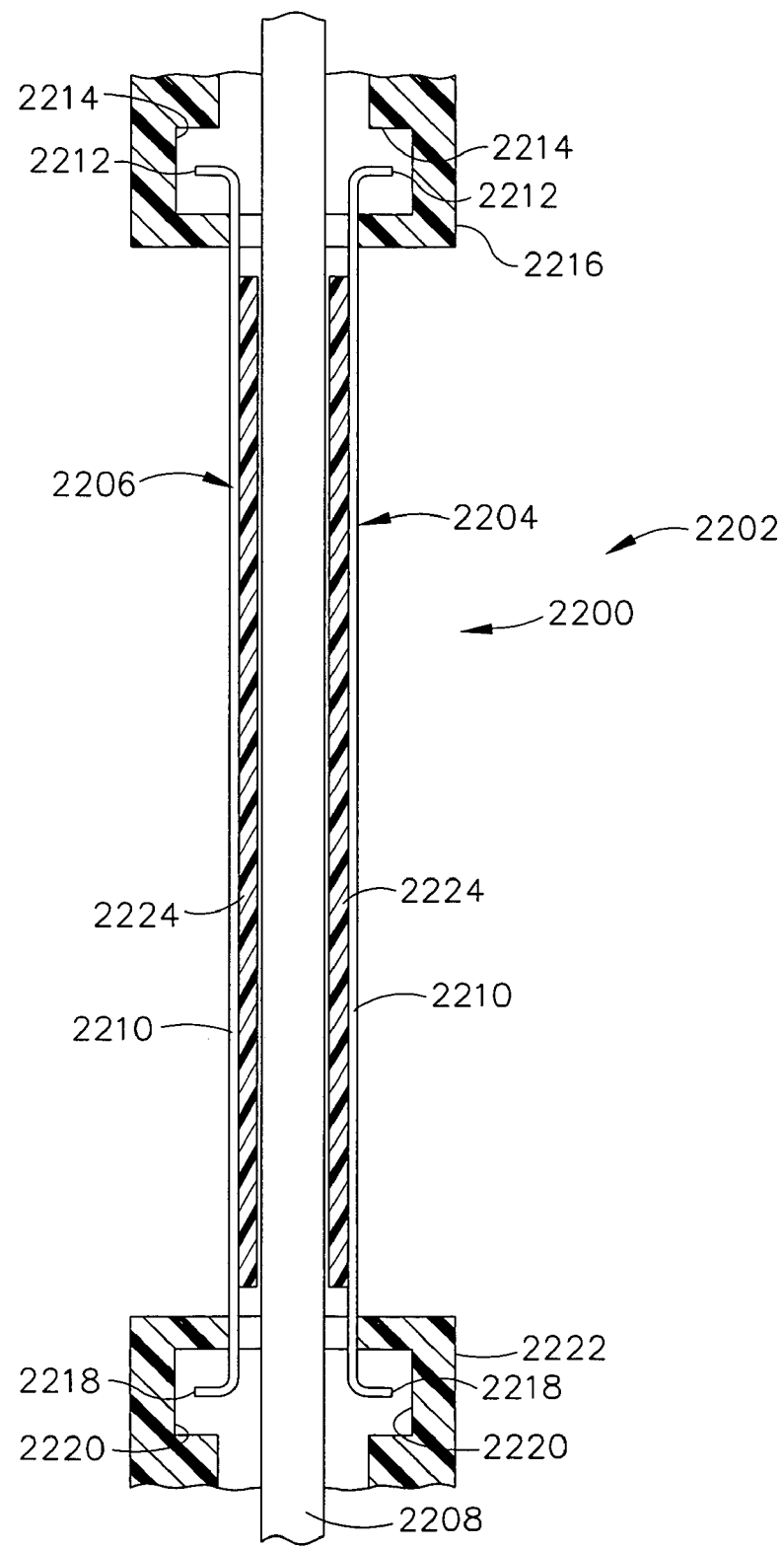
FIG. 19 is a top view taken in longitudinal cross section of a firing bar passing through an articulation joint of a surgical instrument with the firing bar advantageously laterally guided by outwardly actuated EAP support plates having constrained but longitudinally floating hooked ends.

In FIG. 19, an additional alternative articulation joint 2200 for a surgical instrument 2202 includes a pair of EAP support plates 2204, 2206 that laterally support a firing bar 2208 to minimize binding and buckling when articulated. Each support plate 2204, 2206 includes a structural member 2210 (e.g., metal) that includes a first outwardly tabbed end 2212 that is constrained and longitudinally free floating within a first inwardly open recess 2214 in a first frame ground 2216 and a second outwardly tabbed end 2218 that is constrained and longitudinally free floating within a second inwardly open recess 2220 of a second frame ground 2222. A longitudinally expansive EAP laminate 2224 covers an inner surface of each support plate 2204, 2206.

Figure 20:
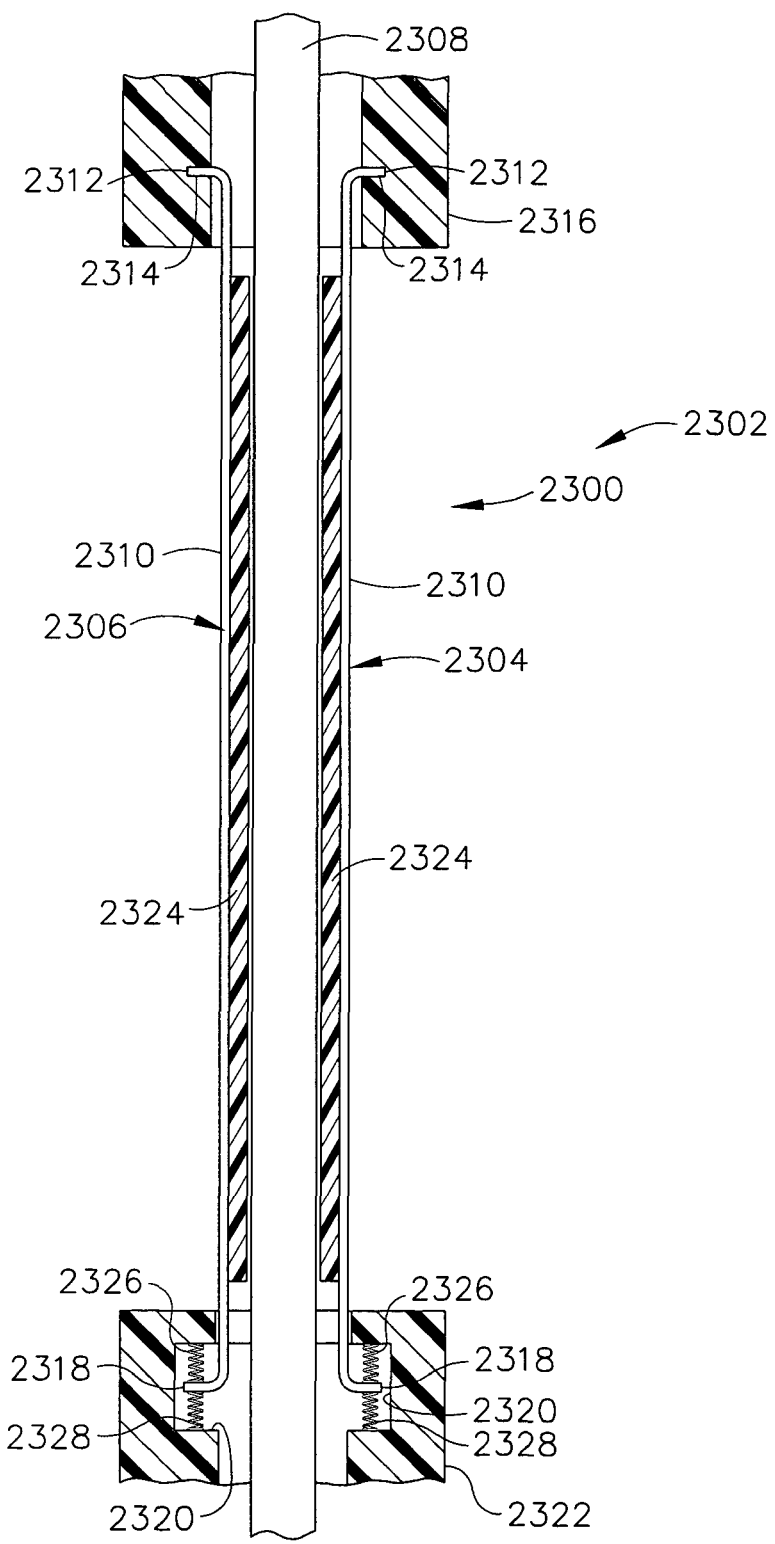
FIG. 20 is a top view taken in longitudinal cross section of a firing bar passing through an articulation joint of a surgical instrument with the firing bar advantageously laterally guided by outwardly actuated EAP support plates each having one fixed hooked end and one end springedly longitudinally constrained.

In FIG. 20, yet an additional alternative articulation joint 2300 for a surgical instrument 2302 includes a pair of EAP support plates 2304, 2306 that laterally support a firing bar 2308 to minimize binding and buckling when articulated. Each support plate 2304, 2306 includes a structural member 2310 (e.g., metal) that includes a first outwardly tabbed end 2312 that is fixed with an inwardly open slot 2314 in a first frame ground 2316 and a second outwardly tabbed end 2318 that is constrained and longitudinally free floating within an inwardly open recess 2320 of a second frame ground 2322. A longitudinally expansive EAP laminate 2324 covers an inner surface of each support plate 2304, 2306. A pair of compression springs 2326, 2328 are longitudinally aligned within the inwardly open recess 2320 biasing the second outwardly tabbed end 2318 of each support plate 2304, 2306 to a neutral position therein.

Figure 21:
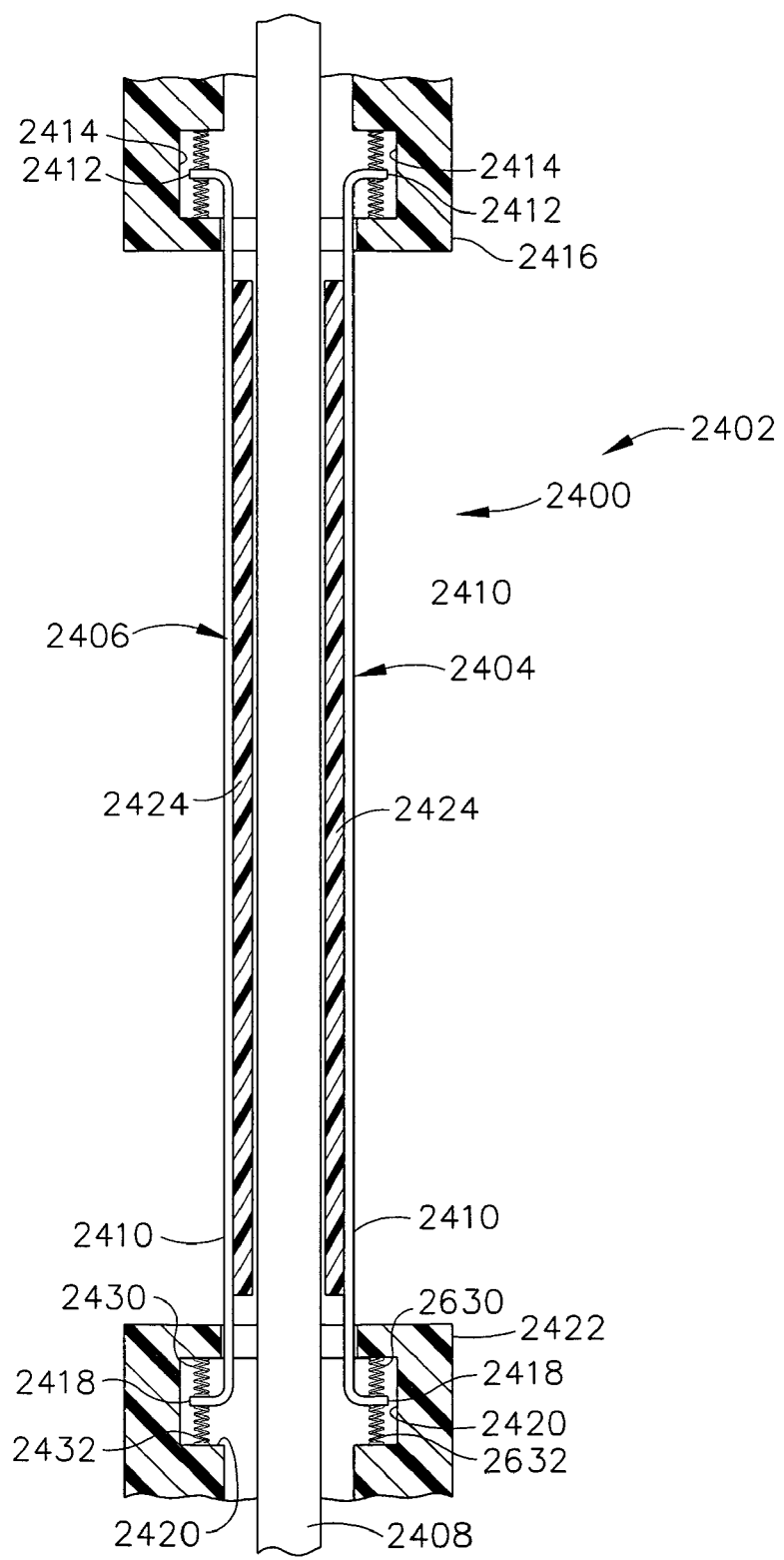
FIG. 21 is a top view taken in longitudinal cross section of a firing bar passing through an articulation joint of a surgical instrument with the firing bar advantageously laterally guided by outwardly actuated EAP support plates with each having both ends springedly longitudinally constrained.

In FIG. 21, yet a further alternative articulation joint 2400 for a surgical instrument 2402 includes a pair of EAP support plates 2404, 2406 that laterally support a firing bar 2408 to minimize binding and buckling when articulated. Each support plate 2404, 2406 includes a structural member 2410 (e.g., metal) that includes a first outwardly tabbed end 2412 that is constrained but longitudinally free floating with a first inwardly open recess 2414 in a first frame ground 2416 and a second outwardly tabbed end 2418 that is constrained and longitudinally free floating within a second inwardly open recess 2420 of a second frame ground 2422. A longitudinally expansive EAP laminate 2424 covers an inner surface of each support plate 2404, 2406. A pair of compression springs 2426, 2428 are longitudinally aligned within the first inwardly open recess 2414 biasing the first outwardly tabbed end 2412 of each support plate 2404, 2406 to a neutral position therein. Another pair of compression springs 2430, 2432 are longitudinally aligned within the second inwardly open recess 2420 biasing the second outwardly tabbed end 2418 of each support plate 2404, 2406 to a neutral position therein.

Figure 24:
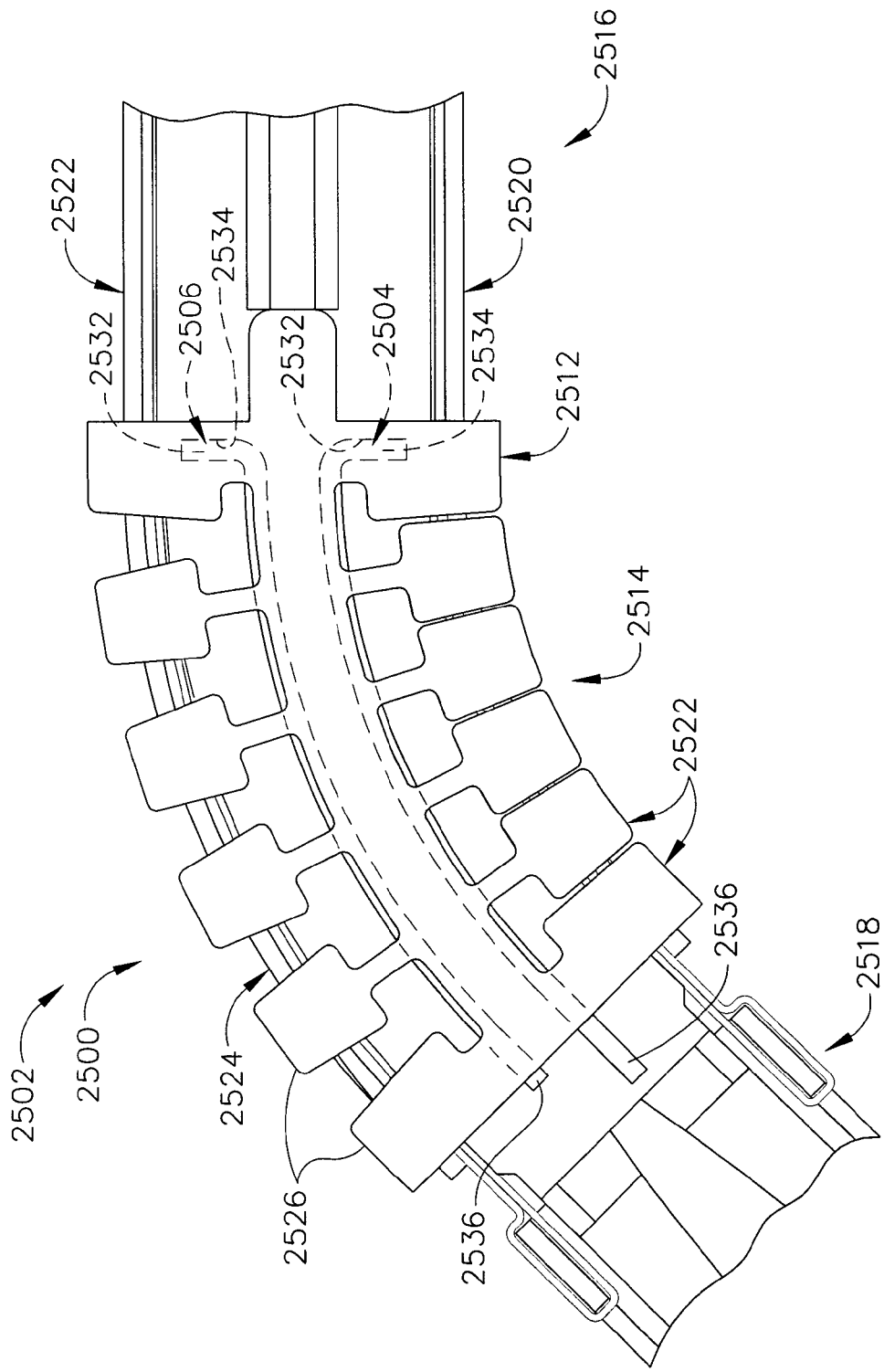
FIG. 24 is a top view of the flexible articulation joint of FIG. 22 articulated to the left.
Figure 25:
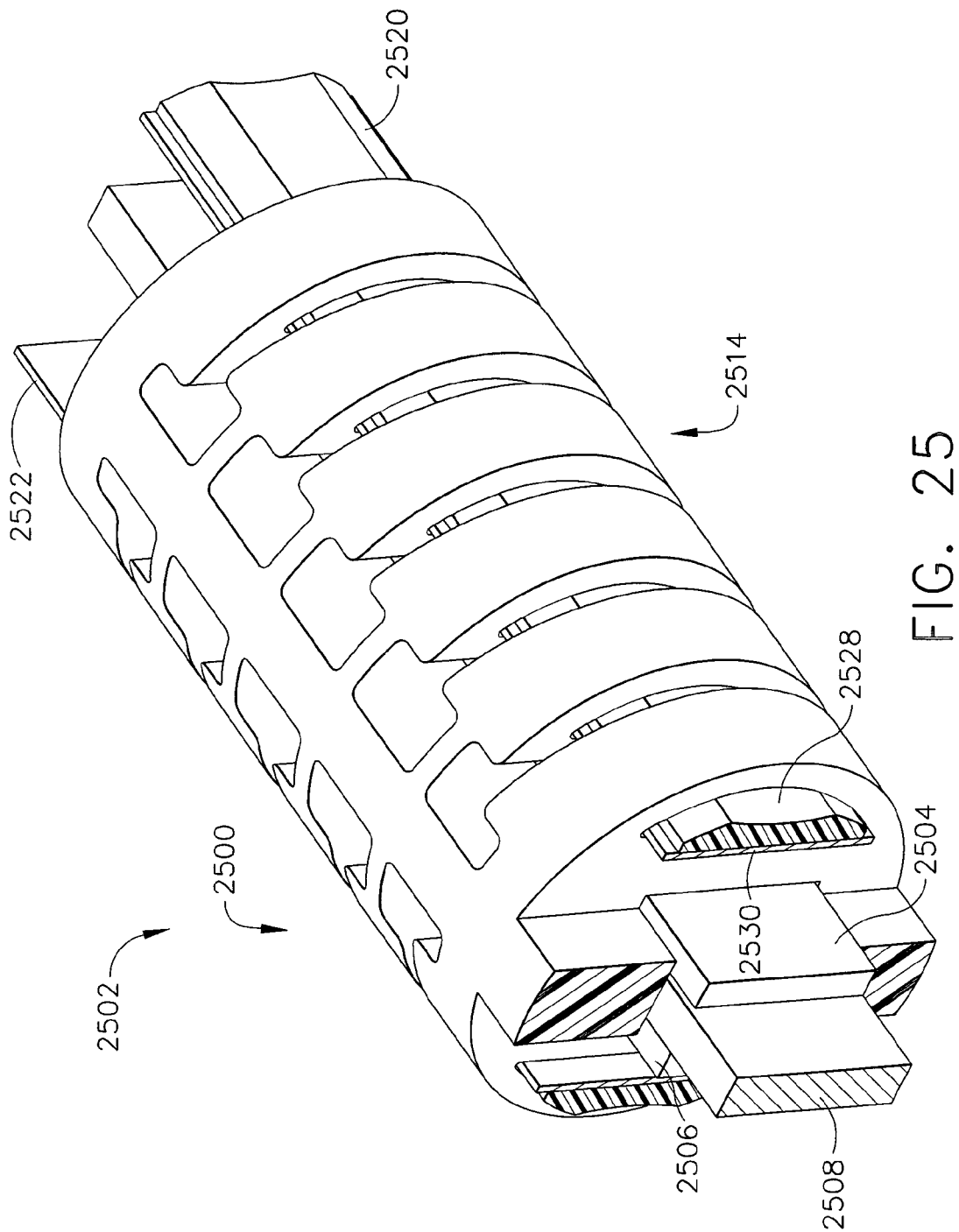
FIG. 25 is a front right perspective view of a flexible articulation joint incorporating the EAP support plates of FIGS. 16-19 and also including left and right EAP plate articulation actuators.

In FIGS. 22-25, yet a further alternative articulation joint 2500 for a surgical instrument 2502 that incorporates EAP support plates 2504, 2506 resides on each lateral side of a firing bar 2508 in a knife slot 2510 of a resilient frame body 2512 of an articulating frame ground 2514 and is proximally coupled to a proximal frame ground 2516 and distally coupled to a distal frame ground 2518. A left EAP plate actuator 2520 passes through a left plurality of lateral ribs 2522 formed in the resilient frame body 2512. A right EAP plate actuator 2524 passes through a right plurality of lateral ribs 2526. Each EAP plate actuator 2520, 2524 extends proximally into the proximal frame ground 2516, includes an outer EAP laminate layer 2528 attached to an inner plate 2530 and is configured to actuate when electrically energized to bend the distal frame round 2518 toward the other side. The resilient frame body 2512 includes proximal inwardly open recesses 2532 that grip proximal, outwardly curved ends 2534 of each support plate 2504, 2506. Distal straight ends 2536 of each support plate 2504, 2506 are allowed to slide out of the knife slot 2510 to adjust for changes in travel for articulation, as depicted in FIG. 24.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. A surgical instrument, comprising:

an end effector;

an elongate shaft defining a longitudinal axis;

an articulation joint comprising an upper band and a lower band each formed of a flexible and longitudinally incompressible material and a plurality of left vertical ribs and a plurality of right vertical ribs, each rib connected on a respective lateral side between the upper and lower bands, the articulation joint further comprising a support plate, wherein the support plate comprises a first portion extending substantially parallel to the longitudinal axis and a second portion extending transverse to the longitudinal axis;

a distal frame ground, wherein the distal frame ground defines an internal recess, wherein the internal recess of the distal frame ground opens transversely relative to the longitudinal recess;

a proximal frame ground, wherein the articulation joint is longitudinally positioned between the distal frame ground and the proximal frame ground, wherein the support plate is engaged with both the distal frame ground and the proximal frame ground, wherein the second portion of the support plate extends into the internal recess of the distal frame ground, wherein the support plate is movable longitudinally relative to one or both of the distal frame ground or the proximal frame ground;
at least one resilient member coupling the support plate with one or both of the distal frame ground or the proximal frame ground, wherein the at least one resilient member is configured to bias the longitudinal position of the support plate relative to one or both of the distal frame ground or the proximal frame ground;
at least one right electroactive polymer actuator attached to the right plurality of vertical ribs and at least one right electroactive polymer actuator attached to the left plurality of vertical ribs, each responsive to an electrical signal to actuate;
a handle portion attached to a proximal end of the elongate shaft and containing control circuitry operatively configured to produce the electrical signal; and
a firing bar proximally attached to the handle portion and movable along the longitudinal axis, wherein the support plate is positioned to laterally support the firing bar through the articulation joint.

2. The surgical instrument of claim 1, wherein the left plurality of ribs includes a left longitudinal actuator recess that receives the left electroactive polymer actuator, the right plurality of ribs including a right longitudinal actuator recess that receives the right electroactive polymer actuator.

3. The surgical instrument of claim 2, wherein the left and right electroactive polymer actuators each comprise a plate actuator operably configured to bend in at least one lateral direction when energized.

4. The surgical instrument of claim 2, wherein the left and right electroactive polymer actuators each comprise at least one electroactive polymer fiber actuator operably configured to longitudinally contract when activated, the respective distal and proximal ends of the left and right electroactive polymer fiber actuators being attached to respective distal and proximal ends of the articulation joint.

5. The surgical instrument of claim 1, wherein the end effector comprises a lower jaw and a pivotally attached upper jaw.

6. The surgical instrument of claim 5, wherein the end effector further comprises a stapling and severing assembly actuated by the firing bar, the handle portion operably configured to impart longitudinal firing motion to the firing bar.

7. The surgical instrument of claim 6, wherein the lower jaw comprises an elongate channel containing a staple cartridge and the pivotally attached upper jaw comprises an anvil presenting a staple forming surface.

8. A surgical instrument, comprising:
an elongate shaft comprising a frame assembly, the elongate shaft defining a longitudinal axis;
a staple applying assembly comprising an elongate channel, a staple cartridge engaged in the elongate channel, and an anvil pivotally attached to the elongate channel presenting a staple forming surface to the staple cartridge;
an articulation joint formed in the frame assembly, the frame assembly comprising a distal frame portion attached to the elongate channel and a proximal frame portion pivotally attached to the distal frame portion, the articulation joint further comprising a support plate, wherein the support plate comprises a first portion extending substantially parallel to the longitudinal axis and a second portion extending transverse to the longitudinal axis, wherein the support plate is engaged with both the distal frame portion and the proximal frame portion, wherein the second portion of the support plate extends into the proximal frame portion or the distal frame portion;
a resilient member securing the second portion of the support plate to the proximal frame portion or the distal frame portion, wherein the resilient member is configured to bias the longitudinal position of the support plate relative to one or both of the distal frame portion or the proximal frame portion;
a handle portion attached to a proximal end of the elongate shaft and operatively configured to selectively communicate an electrical signal to the elongate shaft;
an electroactive polymer actuator connected to the articulation joint and responsive to the electrical signal to perform articulation of the staple applying assembly;
a firing bar proximally attached to the handle portion and movable along the longitudinal axis, wherein the support plate is positioned to laterally support the firing bar through the articulation joint.

9. A surgical instrument, comprising:
an end effector, wherein the end effector defines a longitudinal axis;
an elongate shaft;
a distal frame ground, wherein the end effector is coupled with the distal frame ground;
a proximal frame ground, wherein the elongate shaft is coupled with the proximal frame ground;
an articulation joint attached between the distal frame ground and the proximal frame ground, wherein the articulation joint comprises a support plate, wherein the support plate comprises a first portion extending substantially parallel to the longitudinal axis and a second portion extending transverse to the longitudinal axis, wherein the support plate is engaged with both the distal frame ground and the proximal frame ground, wherein the second portion of the support plate extends into the proximal frame ground or the distal frame ground, wherein the support plate is movable longitudinally relative to one or both of the distal frame ground or the proximal frame ground;
at least one resilient member coupling the second portion of the support plate with one or both of the distal frame ground or the proximal frame ground, wherein the at least one resilient member is configured to bias the longitudinal position of the support plate relative to one or both of the distal frame ground or the proximal frame ground;
a means for electrically actuating the articulation joint;
a handle portion attached to a proximal end of the elongate shaft;
a firing bar proximally attached to the handle portion, wherein the firing bar is movable along the longitudinal axis, wherein the support plate is positioned to laterally support the firing bar through the articulation joint.

10. The surgical instrument of claim 9, wherein the articulation joint comprises a means for supporting the end effector in an arc about a longitudinal axis of the elongate shaft.

11. The surgical instrument of claim 9, wherein the end effector further comprises a stapling and severing assembly actuated by the firing bar, the handle portion operably configured to impart longitudinal firing motion to the firing bar.

12. The surgical instrument of claim 11, wherein the lower jaw comprises an elongate channel containing a staple cartridge and the pivotally attached upper jaw comprises an anvil presenting a staple forming surface.

* * * * *